United States Patent
Sato et al.

(10) Patent No.: US 8,691,146 B2
(45) Date of Patent: Apr. 8, 2014

(54) ELECTRON BEAM STERILIZATION METHOD

(75) Inventors: Yasuko Sato, Tokyo (JP); Ryo Komura, Tokyo (JP); Takayuki Yano, Tokyo (JP); Toshinori Koizumi, Tokyo (JP)

(73) Assignee: Asahi Kasei Medical Co., Ltd., Tokyo (JP)

( * ) Notice: Subject to any disclaimer, the term of this patent is extended or adjusted under 35 U.S.C. 154(b) by 980 days.

(21) Appl. No.: 12/671,270

(22) PCT Filed: Aug. 1, 2008

(86) PCT No.: PCT/JP2008/063878
§ 371 (c)(1),
(2), (4) Date: Mar. 26, 2010

(87) PCT Pub. No.: WO2009/017227
PCT Pub. Date: Feb. 5, 2009

(65) Prior Publication Data
US 2010/0193387 A1    Aug. 5, 2010

(30) Foreign Application Priority Data

Aug. 1, 2007 (JP) ................ 2007-200995
Mar. 31, 2008 (JP) ................ 2008-090609

(51) Int. Cl.
*A61L 2/00* (2006.01)
*B01J 19/08* (2006.01)
*G01N 21/00* (2006.01)

(52) U.S. Cl.
USPC ....... 422/22; 422/1; 422/186.05; 250/453.11; 250/455.11; 250/492.3

(58) Field of Classification Search
USPC ......... 422/1, 22, 186.05; 250/453.11, 455.11, 250/492.3; 606/191, 194, 198; 600/434, 600/585
See application file for complete search history.

(56) References Cited

U.S. PATENT DOCUMENTS 6,617,596 B1    9/2003    Korenev
7,959,857 B2 *  6/2011    Freeman et al. ............ 422/22

(Continued)

FOREIGN PATENT DOCUMENTS

JP    63-65865    3/1988
JP    8-275991    10/1996

(Continued)

OTHER PUBLICATIONS

Japanese patent office English translation of the "Detailed Description" of JP 2006 305296.*

(Continued)

*Primary Examiner* — Monzer R Chorbaji
(74) *Attorney, Agent, or Firm* — Greenblum & Bernstein, P.L.C.

(57) ABSTRACT

To provide an efficient sterilization method for inexpensively sterilizing a medical article having a complex shape such as a body fluid treatment device of a generally-called dry or semi-dry type by so applying an electron beam that the overall absorbed dose distribution is small and to provide its application package form. [MEANS FOR SOLVING PROBLEMS] A method for sterilizing tubular body fluid treatment devices of a dry or semi-dry type contained in an electron beam-transmitting case with an electron beam. The method is characterized in that a stack structure which includes a gap layer having an average density of 0.010 to 0.180 g/cm³ and two body fluid treatment device layers having an average density of 0.050 to 0.200 g/cm³ and sandwiching the gap layer is contained in the electron beam-transmitting case, and the case is irradiated with the electron beam.

17 Claims, 20 Drawing Sheets

(56) References Cited

U.S. PATENT DOCUMENTS

| | | | |
|---|---|---|---|
| 2003/0021722 A1* | 1/2003 | Allen et al. ................ 422/22 |
| 2003/0194344 A1 | 10/2003 | Brafford et al. |
| 2008/0087599 A1 | 4/2008 | Mabuchi et al. |
| 2008/0245723 A1 | 10/2008 | Komura et al. |
| 2010/0062412 A1 | 3/2010 | Nirasawa et al. |

FOREIGN PATENT DOCUMENTS

| | | | |
|---|---|---|---|
| JP | 2000-135274 | 5/2000 | |
| JP | 3076080 | 8/2000 | |
| JP | 2000-325435 | 11/2000 | |
| JP | 2000-325438 | 11/2000 | |
| JP | 2000-325439 | 11/2000 | |
| JP | 2000-334028 | 12/2000 | |
| JP | 2002-000704 | 1/2002 | |
| JP | 2002-078780 | 3/2002 | |
| JP | 3432240 | 8/2003 | |
| JP | 2003-245526 | 9/2003 | |
| JP | 2006 305296 | * 11/2006 | ............ A61M 1/18 |
| WO | 02/061464 | 8/2002 | |
| WO | 03/009875 | 2/2003 | |
| WO | 2006/041125 | 4/2006 | |
| WO | 2006/104082 | 10/2006 | |
| WO | 2007/018242 | 2/2007 | |

OTHER PUBLICATIONS

International Search Report mailed Oct. 21, 2008 that issued with respect to PCT/JP2008/063878.

International Preliminary Report on Patentability, including the Written Opinion (in English) mailed Mar. 4, 2010 that issued with respect to PCT/JP2008/063878.

* cited by examiner (a)

(b)

(a)

(b)

(c)

Example 1

Example 2

Example 3

Example 4

Example 5

Example 6

Example 7

Example 8

Example 9

Example 10

Comparative example 1

Comparative example 2

Comparative example 3

Comparative example 4

Comparative example 5

Comparative example 6

Comparative example 7

Comparative example 8

ELECTRON BEAM STERILIZATION METHOD

TECHNICAL FIELD

The present invention relates to a method of sterilizing a body fluid treatment device used for medical purposes with an electron beam. More specifically, the present invention relates to a sterilization method of sterilizing a plurality of body fluid treatment devices with an electron beam without increasing an absorbed dose distribution (ratio between a maximum absorbed dose and a minimum absorbed dose), and a body fluid treatment device package and a body fluid treatment device sterilized as such.

BACKGROUND ART

Various body fluid treatment devices have been developed for purposes of performing treatments by extracorporeal circulation blood purification therapies such as hemodialysis, hemofiltration, plasma separation, plasma fractionation and the like, and those devices having improved safety and performance have been put to practical use.

The body fluid treatment devices are roughly classified into a wet type in which the insides of the hollows of the hollow fiber membranes and the space between the hollow fiber membranes and a container are filled with an aqueous medium, and a non-wet type in which an aqueous medium is not filled. The latter may be further classified into a dry type in which membranes have a water content of only about several percent, and a semi-dry type (also may be referred to as "half-wet type") in which membranes are moderately wetted with water, a wetting agent or the like. The dry type and semi-dry type body fluid treatment devices have a feature that they have a light product weight and are unlikely to freeze at a low temperature as compared with the wet type body fluid treatment devices. Therefore, the dry type and semi-dry type body fluid treatment devices have a product form particularly excellent in distribution such as transportation and storage.

As a form of packaging these body fluid treatment devices when shipping products, conventionally, body fluid treatment devices are arranged approximately in parallel on a rectangular tray to obtain fixed package intermediates, and the package intermediates are stacked in layers in a rectangular box to obtain a package. The package has been designed paying particular attention to minimizing mechanical damage to the packaged body fluid treatment devices at a time of transportation or falling, and in addition, the package has been designed considering weight reduction, portability, ease of unpacking, and the like.

The body fluid treatment devices are shipped in a sterilized state because they are medical apparatuses. However, if the body fluid treatment devices are packaged after being sterilized one by one, the productivity decreases. Therefore, commonly, the body fluid treatment devices are packaged on one to two dozens basis and thereafter sterilized as a package.

These body fluid treatment devices need to be sterilized completely while being hermetically sealed and packaged before use.

As a method of sterilizing a body fluid treatment device which has been put into practical use, three methods of a gas sterilization method using ethylene oxide gas or the like, an autoclave sterilization method with a high-pressure vapor and a γ-ray irradiation sterilization method have been used mainly. However, in recent years, an electron beam irradiation sterilization method has also become to put into practical use. Of those methods, in regard to the ethylene oxide gas sterilization method, the residual of ethylene oxide gas may cause a problem, which makes it necessary to perform sufficient degassing so as to avoid toxicity. Further, because of prolonged pressurizing and depressurizing a treatment time is repeated, and the performance may be changed depending upon the material. Further, the autoclave sterilization method and the γ-ray irradiation sterilization method have a problem that they are dependent on the properties of the materials constituting a hollow fiber membrane type blood purification device. That is, in the former autoclave sterilization method, the heat resistance in a wet state of a body fluid treatment device is necessary, and depending upon the material, the performance thereof is remarkably degraded during sterilization, which makes it impossible to use the body fluid treatment device. In the latter γ-ray irradiation sterilization method, there are no problems of residual gas and heat resistance, and further, the permeability of an irradiation beam is high. Therefore, the γ-ray irradiation sterilization method is excellent as a method of sterilizing a body fluid treatment device. However, it is well known that a part of a material undergoes a chemical change due to irradiation energy. For example, in a hollow fiber membrane made of a hydrophobic polymer and a hydrophilic polymer constituting a body fluid treatment device, a hydrophilic polymer mainly is denatured and degraded to be eluted from the hollow fiber membrane or to cause a structural change due to cross-linking, and consequently, the transmitting performance, strength, or blood compatibility of the membrane may be decreased.

On the other hand, according to the electron beam irradiation sterilization method, there is no concern of residual toxicity as in the ethylene oxide gas sterilization method, and the sterilization treatment time is not so long as in the autoclave sterilization method, the ethylene oxide gas sterilization method and the γ-ray irradiation sterilization method, and the sterilization treatment may be performed in a short time. Further, when the power is turned off, the irradiation is stopped immediately. When using an accelerator of energy less than 10 MeV, it is not necessary to consider the storage of a radioactive material as in a γ-ray irradiation facility, and in terms of environment the safety is high and a cost is low. Further, a large difference from the γ-ray irradiation lies in that the increase in temperature and the material deterioration of the irradiation object during sterilization are small. Therefore, there is such an advantage as wider selection range of materials, and the further practical use is expected in the future.

However, an electron beam has a smaller permeability to an object compared with a γ-ray, and a transmission distance thereof depends upon the density of the substance to be irradiated. Therefore, conventionally, an electron beam has been practically used only for those which have a relatively uniform shape and are made of a single material, such as surgical gloves and a surgical gown. For example, when an electron beam is irradiated to a body fluid treatment device including a region with a large thickness and a high density, a region where the permeability is insufficient is caused, which increases an absorbed dose distribution (ratio between a maximum absorbed dose and a minimum absorbed dose) between the respective regions in one product. Consequently, problems such as the material deterioration and the eluate may become conspicuous. Specifically, when an irradiation standard is adjusted to the maximum absorbed dose, sterilization at a minimum absorbed dose position becomes insufficient. In contrast, when sterilization is attempted to perform certainly with the irradiation standard being adjusted to the minimum absorbed dose region, the maximum absorbed dose position is irradiated excessively, causing the deterioration and coloring of a material. When the material deterioration such as the decomposition, cross-linking and the like occurs in a hydrophilic polymer, the hydrophilicity of a membrane is impaired, which consequently leads to the decrease in blood compatibility. Thus, depending upon an object to be irradiated, it is not easy to apply an electron beam with small fluctuation in absorbed dose, and there accompanies a problem due to irradiation nonuniformity.

Then, in order to reduce the material deterioration due to the irradiation of an electron beam to an object in a complex shape, study has been conducted mainly from two points of views, that is, in a materials chemistry approach and a process improving approach.

As the materials chemistry approach, a number of technologies of kneading additives such as a radical-trapping agent, an antioxidant and the like into a resin material or allowing the additives to coexist in the vicinity of the resin, which have been widely studied as a method of suppressing the deterioration during irradiation of a radiation including an electron beam. According to these methods, there are advantages in that it is not necessary to modify an irradiation facility substantially, that efficient production may be performed even without prolonging a tact time of irradiation, and the like. However, most of the additives cannot be easily adopted for an extracorporeal circulation type body fluid treatment device in terms of the safety, and particularly regarding a hollow fiber membrane type body fluid treatment device, only a few specific improvement measures against the material deterioration at a time of sterilization with only γ-ray among radiations are found (for example, Patent Documents 1, 2, 7, etc.). Further, only regarding the irradiation of an electron beam, the applicant of the present application has found that the deterioration problem is remarkably solved using a hollow fiber membrane having a specified moisture content and adhesion rate to a radical-trapping material (Patent Document 8). However, although these measures are focused on reducing the material deterioration, there is no viewpoint of reducing the deterioration by decreasing the absorbed dose distribution of an electron beam.

On the other hand, regarding the process improving approach, for example, Patent Document 3 discloses a technology of decreasing an absorbed dose distribution using a shield material together with applying an electron beam under a high accelerated voltage when sterilizing a hollow fiber membrane type dialyzer or an artificial lung with an electron beam. Patent Document 4 discloses an irradiation method comprising an entire irradiation step and a partial shielding step. However, in the former, it is necessary to attach a shield material to an over-irradiated portion for each product individually, and hence, it becomes cumbersome to form a shield having a particular absorbed dose and mount to the product, whereby lowering the operation efficiency. Though the latter has tried to improve the problem, the operation efficiency is still low. Further, Patent Document 5 discloses a technology of, when applying an electron beam to a hollow fiber membrane type body fluid treatment device, applying the electron beam from at least three directions in the case where the body fluid treatment device has a specified product of a density and a thickness. Even in this case, it is necessary to apply an electron beam a number of times while rotating an object to be irradiated, and hence, it is difficult to adopt this technology as a method of sterilizing mass produced products.

On the other hand, Patent Document 6 discloses an irradiation method of applying an electron beam while rotating substances to be irradiated which is arranged in a zigzag arrangement by heaving arrangement pitch intervals during irradiation. This method requires a conveyer transportation mechanism for rotation. Particularly, the mechanism to be set in a transportation conveyer exists immediately under the irradiation beam, and therefore, the mechanism is damaged by a radiation due to continuous irradiation, which makes it substantially difficult to use the mechanism. Further, compared with the irradiation in a package housing a plurality of body fluid treatment devices, the number of body fluid treatment devices that may be irradiated per unit time decreases, and the production efficiency decreases from the viewpoint of commercial production, which increases a cost substantially. Thus, it is difficult to adopt this method.

As described above, from both sides of the process improving approach of uniforming the absorbed dose distribution peculiar to the irradiation of an electron beam, as well as the materials chemistry approach using additives and the like, the study has been conducted to prevent the material deterioration due to the irradiation of an electron beam. However, when considering the perspective of the materials chemistry, only the protection of a material is paid attention to, and a viewpoint of improving by decreasing an absorbed dose distribution of an electron beam is lost. On the other hand, when considering the perspective of uniforming the absorbed dose distribution, only a method of irradiating substances to be irradiated individually and a facility therefore are paid attention to, and a viewpoint of considering an object to be irradiated as a package and treating an object to be irradiated efficiently is lost.

Further, from the viewpoint of safety of medical apparatuses, in the case where substances to be irradiated are individually transported on a conveyer and irradiated, the substances to be irradiated fall from a transportation conveyor or come into contact with a conveyer member dynamically, and a sterilization bag is thus damaged, which causes the risk of increasing the number of viable bacteria before sterilization and of not keeping the completeness of sterilization after sterilization. However, when a package housing a plurality of body fluid treatment devices is irradiated, compared with the case where they are sterilized individually, the above-mentioned risk may be substantially reduced for the reason that the package protects the substances to be irradiated.

More specifically, an approach of considering substances to be irradiated as an aggregate, and, by a simple approach, reducing the irradiation fluctuation of an electron beam efficiently (making an absorbed dose distribution uniform), and reducing the material deterioration, which is neither a microscopic materials chemistry approach nor a large-scale process improving approach, has not been known.

Patent Document 1: JP-B-3076080
Patent Document 2: JP-B-3432240
Patent Document 3: JP-A-H08-275991
Patent Document 4: JP-A-2000-334028
Patent Document 5: JP-A-2000-135274
Patent Document 6: JP-A-2000-325439
Patent Document 7: JP-A-2003-245526
Patent Document 8: WO 2007/018242

DISCLOSURE OF THE INVENTION

Problem to be Solved by the Invention

In view of the above-mentioned problems, an object of the present invention is to provide an electron beam sterilization method of sterilizing a plurality of body fluid treatment devices that are housed in a case with an electron beam, capable of decreasing an absorbed dose distribution per body fluid treatment device and an absorbed dose distribution of a plurality of body fluid treatment devices housed in the case and sterilizing the body fluid treatment devices precisely. Another object of the present invention is to provide a body fluid treatment device package and a body fluid treatment device sterilized with an electron beam in such manner.

Means for Solving the Problems

The inventors have studied so as to solve the above-mentioned problems, and found the importance of providing a portion with a low density between body fluid treatment devices housed in an electron beam-permeable case, when irradiating with an electron beam. However, in a body fluid treatment device having a header and a nozzle while having a tubular shape and having a portion with a high density and a portion with a low density provided unevenly in the device, it is difficult to decrease an absorbed dose distribution merely by providing a large gap between the body fluid treatment devices, and further, providing the large gap degrades a packaging efficiency, thereby unpractical. Then, the inventors have further earnestly studied, and as a result, found, when considering the state in which a plurality of tubular body fluid treatment devices are arranged in parallel as one body fluid treatment device layer, the necessity of forming a specified stack structure with a body fluid treatment device layer and a gap layer including no body fluid treatment device and housing the stack structure in a case. Thus, when a plurality of which are in a dry or semi-dry state are housed in a case and sterilized with an electron beam, an absorbed dose distribution of an electron beam in each body fluid treatment device and between body fluid treatment devices is small and the body fluid treatment devices may be efficiently irradiated, whereby the inventors have achieved the present invention.

That is, the present invention provides the following inventions.

(1) A method of sterilizing a plurality of dry or semi-dry body fluid treatment devices with a tubular shape that are housed in an electron beam-permeable case with an electron beam, comprising housing a stack structure in the electron beam-permeable case and thereafter irradiating with an electron beam: the stack structure comprising one gap layer with an average density of 0.010 to 0.180 g/cm$^3$; and two body fluid treatment device layers with an average density of 0.050 to 0.200 g/cm$^3$ in which both surfaces of the gap layer are sandwiched by the body fluid treatment device layers.

(2) A method according to claim 1, wherein each of the body fluid treatment device layers has a configuration in which body fluid treatment devices are arranged substantially in parallel to each other in an axis direction, and arranged in one row or in a plurality of rows in a circular cross-sectional direction.

(3) A method according to claim 1 or 2, wherein on at least one of the body fluid treatment device layers of the stack structure, a gap layer and a body fluid treatment device layer are alternately stacked and housed in a case.

(4) A method according to any one of claims 1 to 3, wherein the case houses at least one stack structure.

(5) A method according to any one of claims 1 to 4, wherein, in the body fluid treatment device layers opposed to each other through the gap layer sandwiched therebetween, the body fluid treatment devices in the body fluid treatment layers are arranged in a zigzag manner in a circular cross-sectional direction.

(6) A method according to any one of claims 1 to 5, wherein, in one of the body fluid treatment device layers, the body fluid treatment devices in rows adjacent to each other are arranged in a zigzag manner in a circular cross-sectional direction.

(7) A method according to any one of claims 1 to 6, wherein an average thickness of at least one gap layer is 10 mm or more to 100 mm or less.

(8) A method according to any one of claims 1 to 7, wherein an average density of one or more body fluid treatment devices constituting the body fluid treatment device layers is 0.200 to 0.350 g/cm$^3$.

(9) A method according to any one of claims 1 to 8, wherein the body fluid treatment device in the tubular shape contains a separation material and a liquid adhesion rate with respect to a dry weight of the separation material is 50 to 400%.

(10) A method according to claim 9, wherein the fluid is a mixture of water and a polyhydric alcohol.

(11) A method according to any one of claims 1 to 10, wherein the body fluid treatment device has a structure in which a hollow fiber membrane bundle made of a hydrophobic polymer and a hydrophilic polymer is filled a container, an end of the bundle is held in the container by a potting layer to form a hollow fiber membrane inside chamber and a hollow fiber membrane outside chamber, the body fluid treatment device has a fluid inlet and outlet which communicate with the hollow fiber membrane inside chamber and another fluid inlet and outlet which communicates with the hollow fiber membrane outside chamber, and a space portion other than a portion occupied by the hollow fiber membrane bundle and fluid in the boy fluid treatment device is occupied by gas with an oxygen concentration of 0.01% or more.

(12) A method according to claim 11, wherein the gas that occupies the space portion other than the portion occupied by the hollow fiber membrane bundle and the fluid in the body fluid treatment device has substantially the same oxygen concentration as the atmosphere.

(13) A method according to any one of claims 1 to 12, comprising using a body fluid treatment device package unit as the body fluid treatment layer, wherein a body fluid treatment device package unit has a structure in which the body fluid treatment devices are fixed substantially parallel to each other in an axis direction on a rectangular electron beam-permeable tray and arranged in a row in a circular cross-sectional direction, at least a part of one side or adjacent two sides of the tray is provided with an obstacle capable of protruding perpendicularly to a horizontal surface of the tray, and a side opposed to the obstacle is provided with a cutout having a thickness equal to or larger than a thickness of the obstacle.

(14) A method according to claim 13, wherein, in the package unit, the body fluid treatment devices are arranged at equal intervals on the tray, and a relationship between a distance A from a circular cross-section center of the body fluid treatment device at one end to an inner wall on one side at which the obstacle is provided in the tray, and a distance B from a circular cross-section center of the body fluid treatment device at another end to an inner wall on the side opposed to the obstacle in the tray is A≠B.

(15) A method according to claim 14, wherein the distance A satisfies A=a+αb+T or A=0.5a+b+T, and the distance B satisfies B=0.5a+b+T or B=a+αb+T (in the equations, "a" is a diameter of the body fluid treatment device, "b" is an arrangement interval of the body fluid treatment devices, "T" is a thickness of the obstacle, and "α" is a constant,) wherein the diameter "a" of the body fluid treatment device is 30 mm to 80 mm, the arrangement interval "b" of the body fluid treatment devices is 1 mm to 80 mm, the thickness "T" of the obstacle is 3 mm to 10 mm, and the constant "α" is 1.0 to 2.0.

(16) A method according to anyone of claims 13 to 15, wherein, when a plurality of the package units are stacked in multiple layers in an electron beam-permeable rectangular packaging case, the package units are alternately stacked and packaged in the state that the obstacles provided to the package units are inverted by 180° in a horizontal direction.

(17) A body fluid treatment device package sterilized with an electron beam by the method according to any one of claims 1 to 16.

Effects of the Invention

An electron beam sterilization method of the present invention exhibits an excellent effect in that, when the state in which a plurality of tubular body fluid treatment devices are arranged in parallel is considered as one layer, and a body fluid treatment device layer and a gap layer are housed in an electron beam-permeable case so as to form a specified stack structure and then irradiated with an electron beam, the body fluid treatment devices are compactly housed as a package, and the absorbed dose distribution of the electron beam in the body fluid treatment devices may become small.

According to this method, it is not necessary to use a shield material for electron beam sterilization and to apply electron beams a number of times from any direction unlike a conventional technology. Therefore, the method has an advantage that a product with a small absorbed dose distribution may be produced in a simple process. Further, because a package housing a plurality of body fluid treatment devices may be sterilized at one time, there is also an effect that production efficiency is excellent. Further, a body fluid treatment device that is an object to be irradiated does not fall directly from a transportation conveyer or does not come into contact with a conveyer member dynamically. Therefore, the completeness of sterilization may also be kept further.

Figure 1:
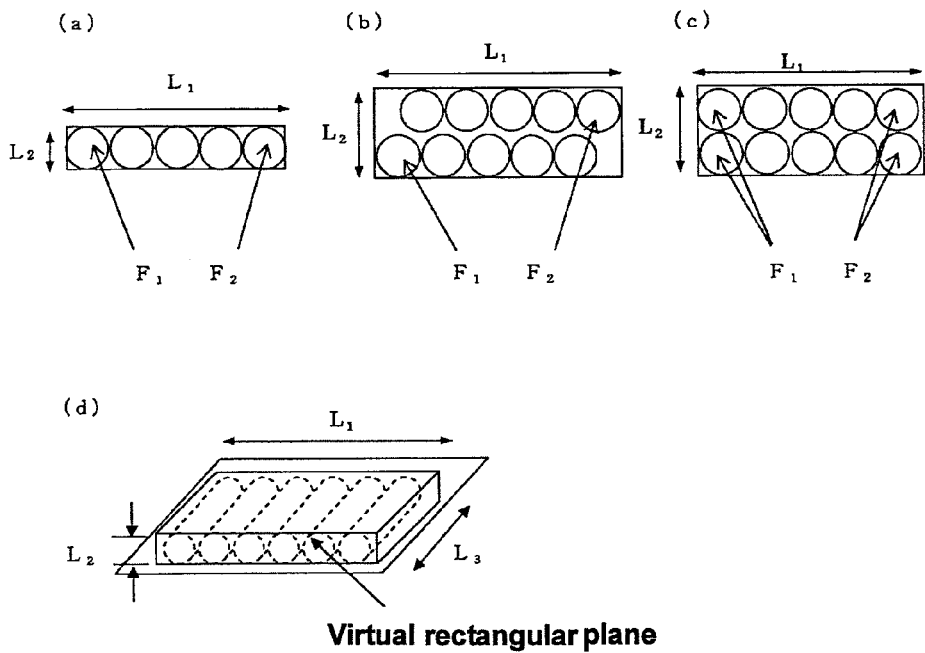
FIG. 1 is a schematic view illustrating one body fluid treatment device layer.

DESCRIPTION OF THE NUMERALS $F_1$, $F_2$: body fluid treatment devices at both ends, of body fluid treatment devices arranged in parallel $L_1$: long side in each outmost peripheral surface of body fluid treatment devices at both ends, of body fluid treatment devices arranged in parallel $L_2$: short side in each outmost peripheral surface of body fluid treatment devices at both ends, of body fluid treatment devices arranged in parallel $L_3$: whole length of body fluid treatment device $L_4$: long side of virtual rectangular plane sandwiched between body fluid treatment device layers in electron beam permeable case $L_5$: short side of virtual rectangular plane sandwiched between body fluid treatment device layers in electron beam permeable case $L_6$, $L_7$, $L_8$, $L_9$: thicknesses at four corners of gap layer $L_{10}$ to $L_{17}$: dimension measurement positions used in Examples and Comparative Examples As to Gs: positions for attaching a dosimeter 1: body fluid treatment device 2: electron beam-permeable rectangular packaging case 3: electron beam-permeable tray 4: package unit (for six-device arrangement with half-width gaps)

5: cutout

6: obstacle a: radius of body fluid treatment device b: interval between body fluid treatment devices A: distance from center of body fluid treatment device at one end to tray end at which obstacle is provided B: distance from center of body fluid treatment device at the other end to tray end S: body fluid treatment device to which dosimeter is attached H: height dimension of obstacle $W_1$: width dimension of obstacle $W_2$: width dimension of obstacle T: thickness dimension of obstacle

BEST MODE FOR CARRYING OUT THE INVENTION

Hereinafter, the present invention is described in more detail.

A body fluid treatment device of the present invention refers to a device with a shape in which a tubular resin container is filled with a filter material such as a hollow fiber membrane, a flat membrane, or a nonwoven fabric, or a separation material such as a porous particulate adsorbent, these materials are held in the container by a potting material, and to which a header having a liquid inlet and outlet port communicated with the inside of the container is installed. The tubular shape is not limited at all and may be a cylindrical shape, a rectangular shape, or the like. More specifically, the body fluid treatment device comprises mainly a tubular body portion filled with a separation material and a header which is attached to one end or both ends of the body portion and has a diameter larger than that of the body portion. The header is provided with about one or two nozzles which function as liquid inlet and outlet ports. The body portion may also be provided with one to three nozzles as liquid inlet and outlet ports. Thus, though the body fluid treatment device has a tubular shape as a whole, it has a complex shape with unevenness in any direction.

The body fluid treatment device is generally called a blood purification device, which is classified into several devices depending upon the kind and the shape of the separation material. Examples thereof include a membrane type hemodialyzer, a hemofilter, a plasma separator, a plasma component fractionator, a nonwoven type or particulate leukocyte remover, a particulate blood or plasma component adsorber and the like, any of which may be used preferably for an extracorporeal circulation method.

The body fluid treatment device is roughly classified into a wet type in which the inside is filled with a liquid and a non-wet type in which the inside is not filled with a liquid. When a large amount of liquid is present inside, the scattering and transmittance of an electron beam may be prevented, and hence, the body fluid treatment device needs to be a non-wet type in order to be sterilized with an electron beam. In particular, the body fluid treatment device needs to be in a dry state in which the water content of the separation material is about several percents, or in a semi-dry state in which the separation material contains moisture, a wetting agent and the like, and the moisture is held at such a degree as not to generate water droplets in an inner wall of the container and the packaging material.

The inventors of the present invention studied and found the following: when a plurality of tubular body fluid treatment devices which are in a above described dry or semi-dry state are housed in a case and sterilized with an electron beam, it is necessary to perform electron beam sterilization after the body fluid treatment devices are housed in an electron beam-permeable case as a stack structure formed of a gap layer with a specified density including no body fluid treatment device and a body fluid treatment device layer with a specified density in which tubular body fluid treatment devices are arranged in parallel.

It has been known until now that, if an absorbed dose distribution of an electron beam in a body fluid treatment device and between body fluid treatment devices is decreased when the body fluid treatment device is sterilized with an electron beam, a region irradiated excessively is relatively reduced to alleviate the local material deterioration. However, the inventors of the present invention studied a simpler method, instead of studying a large-scale facility, and found the following: when a plurality of body fluid treatment devices are housed in a case and sterilized with an electron beam simultaneously, the transmittance and fluctuation in scattering of an electron beam are suppressed and an absorbed dose distribution is decreased by controlling the arrangement of body fluid treatment devices and the gap between body fluid treatment devices.

One body fluid treatment device layer of the present invention refers to a layer in which a plurality of tubular body fluid treatment devices are arranged so that their central axes are substantially parallel to each other substantially on the same plane and the end surfaces of the body fluid treatment devices are located substantially on the same plane. More specifically, as illustrated in FIGS. 1(a) and 1(d), the body fluid treatment device layer refers to a plate-shaped space ($L_1 \times L_2 \times L_3$) determined by a product of a virtual rectangular plane ($L_1 \times L_2$) in which each of body fluid treatment devices at both ends ($F_1$, $F_2$), of the body fluid treatment devices arranged in parallel, is inscribed to a long side ($L_1$) and a short side ($L_2$) in an outmost peripheral surface, and a whole length ($L_3$) of the body fluid treatment device. Further, in the case where the body fluid treatment devices are placed on a tray, the body fluid treatment device layer refers to a plate-shaped space ($L_1 \times L_2 \times L_3$) determined by a product of a virtual rectangular plane ($L_1 \times L_2$) in which the tray and each of body fluid treatment devices are inscribed to a long side ($L_1$) and a short side ($L_2$) in an outmost peripheral surface and a whole length ($L_3$) of the body fluid treatment device (tray). In the case where the body fluid treatment devices are housed in a box or a case, a space partitioned by an outmost peripheral surface of the case or box corresponds to a body fluid treatment device layer.

The body fluid treatment devices arranged in parallel substantially on the same plane may be in two rows or more. In such a case, a virtual rectangular plane is set as shown in FIG. 1(b) or 1(c), and the body fluid treatment device layer is assumed to be a flat-shaped space determined by a product of the virtual rectangular plane and the whole length ($L_3$) of the body fluid treatment devices.

In the present invention, the density of a body fluid treatment device layer is a first important point for decreasing an absorbed dose distribution of an electron beam, and it is necessary that the density be 0.050 to 0.200 g/cm³. The density of the body fluid treatment device layer is a value determined by dividing the weight of a layer in which the body fluid treatment device is arranged by the volume of the body fluid treatment device layer, and is represented by the following Equation (1).

As described later, as the body fluid treatment devices are hermetically sealed at least in sterilization bags one by one and sterilized, the body fluid treatment devices are packaged in sterilization bags respectively when arranged in a body fluid treatment device layer. Further, a support may be used for fixing the body fluid treatment device. In this case, the sterilization bag and the support may also influence the permeability of an electron beam. Therefore, the total weight including the sterilization bags and supports, as well as the body fluid treatment devices constituting the body fluid treatment device layer is used in the equation (1) as the weight of the body fluid treatment device layer. Further, the volume of the body fluid treatment device layer refers to a space volume calculated from $L_1 \times L_2 \times L_3$ of FIG. 1(d).

$$\text{Density of body fluid treatment device layer (g/cm}^3\text{)} = \frac{\text{Weight of body fluid treatment device layer (g)}}{\text{Volume of body fluid treatment device layer (cm}^3\text{)}} \quad (1)$$

If the density of the body fluid treatment device layer is larger than 0.200 g/cm³, the volume occupied by the layer per body fluid treatment device becomes small. Therefore, the permeability of an electron beam is weakened, and the absorbed dose distribution per one body fluid treatment device increases, resulting in an increase in the absorbed dose distribution in one case. The density is more preferably 0.180 g/cm³ or less, and particularly preferably 0.150 g/cm³ or less. On the other hand, if the density of the body fluid treatment device layer is smaller than 0.050 g/cm³, the volume occupied by the layer per body fluid treatment device increases. Therefore, the size of the case increases compared with the case where the same numbers of devices are packaged. Alternatively, the number of housed devices becomes small compared with the case where they are packaged in the same case. In any case, the amount of electron beam irradiation at a time is limited, and irradiation efficiency is reduced. The density is more preferably 0.060 g/cm³ or more, and particularly preferably 0.070 g/cm³ or more.

In the present invention, it is necessary that the body fluid treatment device layer maintains the layer density in a package, at least until the devices are sterilized with an electron beam. There is no particular limit to the means for maintaining the layer density or the layer shape. For example, the body fluid treatment devices may be maintained by arranging in parallel and housing in a tubular or box-shaped support, arranging in parallel on a plate-shaped support having a fixing tool, merely arranging in parallel on a plate-shaped support, or the like. Alternatively, the body fluid treatment devices may also be bound in a row with a band-shaped support. Such a support is preferably capable of fixing the body fluid treatment devices substantially in parallel each other in an axis direction on an electron beam-permeable rectangular tray, and arranging the body fluid treatment devices in a row in a circular cross-sectional direction. In the present invention, one tray on which such body fluid treatment devices are arranged is referred to as a "package unit for body fluid treatment devices", and a plurality of package units stacked and housed in an electron beam-permeable rectangular packaging case, may be referred to as a "package for body fluid treatment devices". As the support, a corrugated cardboard, a pulp mold, a resin foam or the like is preferred due to a low density, and they have less problems as wastes.

In the present invention, it is preferred that the average density of one or more body fluid treatment device constituting the body fluid treatment device layer be 0.200 to 0.350 g/cm³. If the average density is larger than 0.350 g/cm³, the weight of the body fluid treatment device increases, and the absorbed dose distribution per body fluid treatment device increases. When the absorbed dose distribution increases, an absorbed dose per body fluid treatment device increases so as to secure a sterilization property, which allows the material deterioration to proceed. The average density is more preferably 0.345 g/cm³ or less, and particularly preferably 0.340 g/cm³ or less. When considering the minimum size of the body fluid treatment device to be used generally, the lower limit of the density is about 0.200 g/cm³ or more.

Main factors influencing the density of a body fluid treatment device include the volume (diameter, thickness) of a potting portion formed at ends of the body fluid treatment device, a specific gravity, a filling ratio and a liquid adhesion rate of separation material and the like. The density of a body fluid treatment device, and the density of a body fluid treatment device layer by extension may also be controlled even by setting those factors appropriately. Above all, the liquid adhesion rate of the separation material has an advantage of being easily and arbitrarily controlled compared with the basic specifications such as the volume of a potting portion, the specific gravity and filling ratio of the separation material. Further, the effect of protecting the separation material by a liquid may be expected.

In the present invention, a liquid that is a wetting agent may adhere to the separation material in a body fluid treatment device. The wetting agent refers to a liquid component adhering to and covering the whole surface of the separation material and having a function of protecting a hydrophilic polymer constituting the separation material from deterioration during electron beam sterilization.

The function of the wetting agent which prevents a hydrophilic polymer from the deterioration specifically refers to trapping radicals generated in the separation material due to electron beam sterilization (also referred to as "electron beam irradiation") or inhibiting or eliminating the reactivity of radicals by reacting with the radicals.

As typical examples of a compound having such a function, there are exemplified antioxidants such as ascorbic acid, a tocopherol, polyphenols and the like. More specifically, it is desirable to use: vitamins such as vitamin A (derivatives thereof, sodium ascorbate, and palmitol-ascorbate), vitamin C, and vitamin E (derivatives thereof and salts such as tocopherol acetate, α-tocotrienol, or the like); polyhydric alcohols such as glycerol, mannitol, and glycols; saccharides such as glucose, mannose, xylose, ribose, fructose, and trehalose; fatty acids such as oleic acid, furan fatty acid, thioctic acid, linoleic acid, palmitic acid, and salts and derivatives thereof; and the like.

However, the wetting agent more preferably simultaneously satisfies such requirements that the wetting agent has a moderate viscosity and is easily retained on the separation material surface while having a function of preventing a hydrophilic polymer from the deterioration, does not form a strong chemical bond with a hydrophobic polymer or a hydrophilic polymer, and is easily washed with a physiological aqueous solution. Specifically, of the above-exemplified compounds, polyhydric alcohols such as glycerol, mannitol, glycols (e.g., ethylene glycol, diethylene glycol, propylene glycol, and tetraethylene glycol), and polyglycols (e.g., polyethylene glycol) exhibit not only a high radical-trapping capability per molecule but also high solubility in water and physiological solution. Therefore, a polyhydric alcohol aqueous solution easily covers the entire separation material surface and is easily washed away. Accordingly, it is preferable to use aqueous solutions thereof. Of those, an aqueous solution of glycerol or polyethylene glycol is more preferable because glycerol or polyethylene glycol has been already used as a pore size retention agent or a surface modifier for blood purification hollow fibers, and an aqueous solution of glycerol is most preferable.

In the present invention, an adhesion rate of the wetting agent with respect to a dry weight of the separation material, i.e., a liquid adhesion amount is desirably 50% or more and 400% or less. If the liquid adhesion amount is less than 50%, it takes time until hydrophilicity is obtained and air removability is poor during priming performed before actual use in a medical site. Further, the protection effect for the separation material also becomes low, which allows the material deterioration to proceed more easily. The liquid adhesion amount is more preferably 60% or more, and particularly preferably 70% or more. On the other hand, if the liquid adhesion amount is larger than 400%, though the protection effect to the separation material increases, the weight in the case increases due to the increase in weight of the body fluid treatment devices, and the density in the case increases, resulting in an increase in an absorbed dose distribution. Further, tarnishing and water droplets are likely to occur during storage. Thus, the liquid adhesion amount is more preferably 350% or less, and particularly preferably 300% or less. The separation material having the liquid adhesion rate within this range is preferred because it is particularly excellent in ease of handling and product appearance even in a region called a semi-dry.

The adhesion rate of the wetting agent described above is calculated as a total weight of the wetting agent with respect to the dry weight of the separation material. There is no particular limit to a measurement method, but in the case where a wetting agent is fat-soluble, the wetting agent is extracted with a solvent which dissolves the material but does not dissolve the separation material, and is quantified using liquid chromatography, a coloring reagent, and the like. Further, in the case where the wetting agent is a water-soluble material, the wetting agent is extracted with warm water or hot water and quantified similarly. Further, in the case where the wetting agent is an aqueous solution, a moisture content may be calculated separately in accordance with a measurement procedure of a moisture content described later, as a sum of an adhesion rate of a solute portion and a moisture content.

Further, in the present invention, in the case where a liquid that is a wetting agent is a mixture (polyhydric alcohol aqueous solution) of water and a polyhydric alcohol, it is preferred that the ratio of the polyhydric alcohol with respect to water be 0.2 times or more and 7.5 times or less. If the ratio of the polyhydric alcohol with respect to water is larger than 7.5 times, the local concentration of the polyhydric alcohol adhering to the surface of the separation material and the inside of the separation material increases, and an adhesion region becomes viscous. Consequently, the covering state is likely to become non-uniform, which rather makes insufficient the protection effect from the irradiation of an electron beam. Further, the freezing point of a polyhydric alcohol aqueous solution increases, and an aqueous solution contained in the separation material is likely to be frozen. Therefore, damages involving the change in a structure of the separation material are likely to occur. Thus, it is preferred that the ratio of the polyhydric alcohol with respect to water be 7.5 times or less. Particularly, in the case where the polyhydric alcohol is glycerin, the ratio is more preferably 5.7 times or less at which the freezing point of a glycerin aqueous solution becomes −10° C. or less. The ratio is particularly preferably 3 times or less at which the freezing point of a glycerin aqueous solution is −30° C. or less.

On the other hand, it is preferred that the lower limit be 0.2 times from the viewpoint of the protection effect. Particularly, in the case where the polyhydric alcohol is glycerin, the lower limit is more preferably 0.5 times or more at which the freezing point of a glycerin aqueous solution is −10° or less, and particularly preferably 1.2 times or more at which the freezing point of the glycerin aqueous solution is −30° C. or less. The ratio of the polyhydric alcohol with respect to water is determined from the following Equation (2).

$$\text{Ratio of the polyhydric alcohol with respect to water} = \frac{\text{Weight of glycerin (g)}}{\text{Weight of water (g)}} \quad (2)$$

In the present invention, when the wetting agent is a polyhydric alcohol aqueous solution, it is preferred that the separation material in the body fluid treatment devices is adhered with a polyhydric alcohol of 10% or more and 300% or less with respect to the dry weight of the separation material. In the case where the polyhydric alcohol adheres as an aqueous solution, the ratio of the net weight of the polyhydric alcohol excluding a water component with respect to the dry weight of the separation material is used for an adhesion rate of the polyhydric alcohol.

Here, if the adhesion rate of the polyhydric alcohol with respect to the dry weight of the separation material exceeds 300%, the weight of the body fluid treatment device increases, the advantages of the semi-dry type body fluid treatment device are spoiled, and the handling properties are lost. There is an increased tendency of liquid droplets to adhere to the inner wall of the container and the inside of a sterilization bag at about room temperature (e.g., about 20 to 40° C.), at which the body fluid treatment device is generally stored and distributed, whereby the appearance of the product deteriorates. Further, the concentration of polyhydric alcohol that adheres to the surface and the inside of the separation material locally increases, whereby the viscosity of the region to which the polyhydric alcohol adheres increases. As a result, the covering state tends to easily become non-uniform, whereby the protection effect from the electron beam irradiation becomes insufficient on the contrary. On the other hand, there is a problem on the production method. Specifically, when assembling after the adhesion rate is adjusted in a state of a bundle, the adherence property of the outer surface of the separation materials increases, whereby the separation materials tend to bond to each other. As a result, the potting agent is prevented from entering, whereby leakage may occur. When the adhesion rate is adjusted after assembly, dialysis efficiency may be disturbed when bonding between the separation materials occurs. Therefore, the adhesion rate of polyhydric alcohol is preferably 300% or less, more preferably 250% or less, and particularly preferably 200% or less.

On the other hand, the adhesion rate of 10% or more is preferred as a lower limit from the viewpoint of the protection effect. According to the finding by the inventors of the present invention, 80% or more of the adhesion rate of polyhydric alcohol is required in the case where γ-ray irradiation is involved. However, the damage given to a hydrophilic polymer of the separation material by an electron beam is small, and hence, the lower limit may be decreased to 10% in the present invention. When the adhesion rate of the polyhydric alcohol is lowered as such, the density of the entire separation material decreases, which may further decrease a dose distribution of an electron beam. Further, in a priming operation before use, the polyhydric alcohol may be removed rapidly and precisely. The adhesion rate is more preferably 50% or more and particularly preferably 80% or more from the viewpoint of the effect of protecting from the deterioration in the separation material.

In the present invention, the adhesion rate of polyhydric alcohol is preferably within the above-mentioned range, and simultaneously the ratio of the amount of water in the separation material with respect to the dry weight of the separation material, that is, the water content is preferably 40% or more and less than 100%. If the water content is 40% or more, activation of platelets may be suppressed in the initial stage of contact with blood. The detailed reason is not certain, but considered to be as follows. A hydrophilic polymer is hydrated when the surface of the separation material is moderately wetted, and the separation material exhibits increased wettability in the initial stage of use as compared with an extremely dried separation material, whereby affinity to blood may increase. This is a very important feature when it is necessary to use a semi-dry type blood purification device immediately after priming. However, if the water content is 100% or more, water contained in the pores of the separation material freezes even if water does not exist around the separation material, whereby damage accompanying a change in structure of the separation material tends to occur. In addition, if the water content exceeds the equilibrium water content of the separation material, excess water tends to adhere to the inner wall of the container or the inside of the sterilization bag as water droplets, whereby the appearance of the product deteriorates.

On the other hand, if the water content is less than 40%, platelets become active in the initial stage of contact with blood, whereby blood compatibility tends to decrease. The reason therefor is considered to be as follows. Because the molecular mobility of the hydrophilic polymer decreases if the surface of the separation material is in an extremely dry state, it takes time for the hydrophilic polymer to get wetted with water and change into a hydrated state when the body fluid treatment device is used. In particular, when the wetting agent is polyhydric alcohol, because the fluctuation in the adhesion rate of polyhydric alcohol to the separation material increases due to an increase in viscosity, separation materials with an extremely low hydrophilicity tend to be obtained. As a result, blood compatibility tends to decrease. Considering the fact that a powder or a high-concentration solution of the hydrophilic polymer does not dissolve in water at once, and it takes time to dissolve, the above estimation may be highly appropriate. It is more preferable that the water content be 60% or more.

In the present invention, the adhesion rate of polyhydric alcohol and water content are measured by the following method. 5 g of a separation material are collected from the body fluid treatment device and the weight (A) of the separation material before drying is accurately measured. After removing only water using a vacuum dryer, the weight (B) of the separation material after drying is measured.

Then, a separation material sample after drying from which only water has been removed is used, and the whole separation material sample is finely cut. After the addition of 300 ml of pure water to the finely cut samples, the samples are sealed and washed for 60 minutes using an ultrasonic washing device to extract adhering polyhydric alcohol. The amount of the polyhydric alcohol (C) is determined as follows. The extract obtained by subjecting the cut separation material sample to extraction using the ultrasonic washing device is subjected to quantitative determination by liquid chromatography. A calibration curve is obtained from the peak area of a standard solution, and the amount of the polyhydric alcohol (C) in the extract is determined using the above-mentioned calibration curve. Further, only the cut separation material sample is taken out from the extract and is dried using a vacuum dryer. The weight of the dried cut separation material sample is measured and taken as the weight (D) of the separation material to which polyhydric alcohol and water do not adhere.

The water content is calculated by the following equation (3) based on the above-mentioned measured values, and adhesion rate of the polyhydric alcohol is calculated by the following equation (4).

The polyhydric alcohol adhesion rate may also be determined by $\{(B-D)/D\} \times 100$. Further, the adhesion rate of the wetting agent may also be determined from the total of the water content and the polyhydric alcohol adhesion rate determined in the following. Further, the adhesion rate may also be determined by $\{(A-D)/D\} \times 100$. The eater content is determined by Equation (3), and the polyhydric alcohol adhesion rate is determined by Equation (4). The adhesion rate of a wetting agent is determined by summing them up.

$$\text{Water content (wt \%)} = \{(A-B)/D\} \times 100 \quad (3)$$

$$\text{Polyhydric alcohol adhesion rate (wt \%)} = (C/D) \times 100 \quad (4)$$

The definition and preferred characteristics of the body fluid treatment device layer are as described above. Suppressing the material deterioration further using another means has an important meaning as a method of sterilizing a medical apparatus for decreasing an absorbed dose distribution between body fluid treatment devices to reduce the material deterioration. Therefore, in the present invention, it is preferred to control an oxygen concentration in the body fluid treatment device, which is, as a result, important for taking balance between the generation of an eluate from the separation material and the blood compatibility. As for the oxygen concentration in the body fluid treatment device, the lower, the better, because cutting a polymer main chain caused by the generation of an oxygen radical due to the electron beam irradiation, i.e., the oxidative decomposition, may be suppressed, which may suppress the deterioration of the separation material consequently. On the other hand, in the case where the separation material contains a hydrophilic polymer, the cross-linking of the hydrophilic polymer proceeds to denature the surface of the separation material, which may decrease the blood compatibility to a large extent. There is also a problem that a tubular container and header are colored, in addition to the problem that the separation material is denatured.

However, because the body fluid treatment device is covered with a predetermined wetting agent, the above problem caused by oxygen may be remediated without deoxidation particularly even though electron beam sterilization is performed. More specifically, the oxidative decomposition of the separation material may be suppressed even under an atmospheric condition. Further, the cross-linking of a hydrophilic polymer contained in the separation material, and the coloring of the tubular container and header may also be suppressed.

Further, if the inside of the body fluid treatment device is deoxidized, the oxidative decomposition of the separation material may further be suppressed. In this case, it is necessary that at least a space portion in the body fluid treatment device other than that occupied by the separation material and the wetting agent is occupied by a gas with an oxygen concentration of 0.01% or more. When the oxygen concentration in the gas is 0.01% or more, the deterioration in a hydrophilic polymer contained in the separation material is suppressed and an eluate is suppressed to be low, and simultaneously, the excessive cross-linking of the hydrophilic polymer is inhibited. Therefore, excellent blood compatibility is obtained. Further, even if the container and the header are colored, which is just temporary, and will be discolored soon during the storage. On the other hand, if the oxygen concentration is less than 0.01%, is not preferred because the coloring of the container and header are hardly discolored and consequently the product appearance unpreferably becomes worse.

More preferably, the oxygen concentration in the gas is set to be substantially the same as that of the atmosphere. The oxygen concentration that is substantially the same as that of the atmosphere means here 20.0 to 22.0% in consideration of measurement fluctuation. In the present invention, the separation material is sterilized with an electron beam while being covered with a wetting agent. Therefore, even if the oxygen concentration is higher than that in the radiation sterilization step in the conventionally general deoxidized state, the deterioration of the separation material is suppressed sufficiently. Thus, special members such as a deoxidizer, an oxygen impermeable packaging material and the like, which are conventionally used together in radiation sterilization, become unnecessary. Further, the step of sealing inactive gas, nitrogen gas or the like in a space portion is not required. Thus, it is very preferred.

The number of body fluid treatment devices to be arranged in parallel substantially on the same plane in a body fluid treatment device layer is not particularly limited. The case size of a commercially available body fluid treatment device is about 250 to 400 mm (length)×300 to 650 mm (width)×100 to 370 mm (height), the size is obtained considering the portability and a storage place during a production step, a transportation step, or in a medical facility, the maximum diameter of the body fluid treatment devices is about 3 to 8 cm, and the nozzle length is about 3 cm. Considering those facts, 4 to 12 body fluid treatment devices may be arranged in one row in the layer. Further, a width ($L_2$) of the body fluid treatment device layer may be 3 to 25 cm in view of the maximum diameter, preferably 3 to 17 cm.

Figure 2:
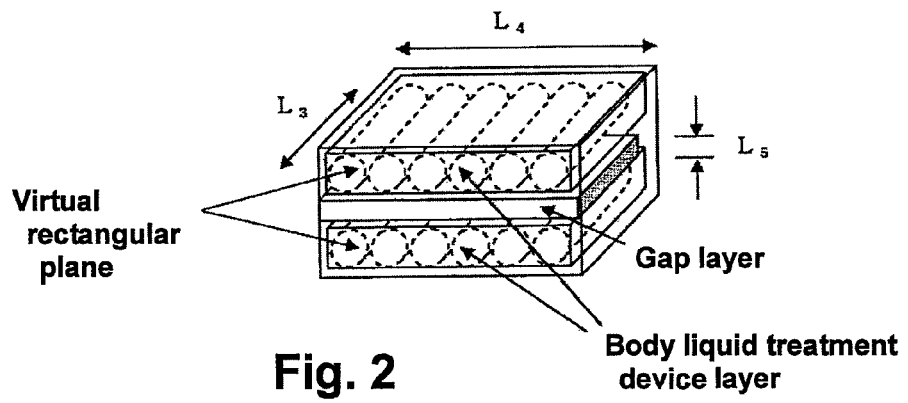
FIG. 2 is a schematic view illustrating a gap layer.

The gap layer as used herein refers to a layer which is sandwiched between two body fluid treatment device layers to separate the body fluid treatment device layers and in which a body fluid treatment device is not present. More specifically, as illustrated in FIG. 2, the gap layer refers to a plate-shaped space ($L_3 \times L_4 \times L_5$) determined by a product of a virtual rectangular plane ($L_4 \times L_5$) sandwiched between the body fluid treatment device layers in an electron beam-permeable case and a whole length ($L_3$) of the adjacent body fluid treatment device layer.

In the present invention, the density of the gap layer is a second important point for suppressing an absorbed dose distribution of an electron beam, and needs to be 0.010 to 0.180 g/cm$^3$. The density of the gap layer is a value determined by dividing the weight of the gap layer by the volume of the gap layer and is represented by the following Equation (5). As described later, the gap layer is not a mere space, and is formed of paper and a resin material for holding a certain shape. The gap layer may influence the permeability of an electron beam, and hence, in Equation (5), the total weight including the material forming the gap layer is used as the weight of the gap layer. Further, the volume of the gap layer refers to a space volume calculated from $L_4 \times L_5 \times L_3$ of FIG. 2.

$$\text{Density of gap layer (g/cm}^3\text{)} = \frac{\text{Weight of gap layer (g)}}{\text{Volume of gap layer (cm}^3\text{)}} \quad (5)$$

When the density of the gap layer is larger than 0.180 g/cm$^3$, the permeability of an electron beam is weakened, and an absorbed dose distribution in one case increases. When an absorbed dose distribution increases, an absorbed dose per body fluid treatment device becomes high, which allows the material deterioration to proceed. The density of the gap layer is more preferably 0.170 g/cm$^3$ or less, and particularly preferably 0.160 g/cm$^3$ or less. In contrast, in order to get the density to be lower than 0.010 g/cm$^3$, it is necessary to replace the material for the gap layer with a lighter one or to increase the width of the gap layer. Thus, the volume occupied by one body fluid treatment device increases, and the case size increases compared with the case where the same number of devices are packaged, and the dose of irradiation at a time is limited, resulting in a reduction in an irradiation efficiency. The density of the gap layer is more preferably 0.012 g/cm$^3$ or more, and particularly preferably 0.013 g/cm$^3$ or more.

The gap layer is not a mere space and separates two body fluid treatment device layers at a predetermined distance in an electron beam-permeable case. Therefore, the gap layer may be formed of a material, which does not hinder the permeability of an electron beam remarkably and is inexpensive, in a shape of a cube or a rectangular solid. From the viewpoint of maintaining the strength of a formed body, the gap layer is preferably formed of a cardboard or a pulp mold if it is made of paper, or formed of a thin plate mold or foamed polystyrene if it is made of a resin. Further, the gap layer may be formed of an appropriate combination thereof. The gap layer may have a box shape in which all the 6 surfaces are made of the forming material or may lack two surfaces. The inside of the gap layer is filled uniformly or hollow, and in the case of hollow, a support structure for preventing deformation may be provided inside.

Further, the gap layer also has the ability to absorb shock necessary for the case where an electron beam-permeable case housing the product falls during the production step, the transportation/transfer and the like, and thus the damage to a sterilization bag packaging the product and the damage to the product may be reduced remarkably. Particularly for the medical apparatus such as a blood purification device, the gap layer is effective for assuring the safety of the product more highly. Even in the case of using a support made of a conventionally available pulp mold or cardboard, a gap may be formed in the case by floating a body fluid treatment device, or the function of absorbing shock may be provided. However, it is difficult for those methods to ensure a particular gap layer that suppresses a fluctuation in irradiation. Further, according to those methods, fixing of a body fluid treatment device is mainly focused, and the absorption of shock received from the upper and lower directions under the condition that the body fluid treatment devices are packaged in a box is not particularly considered. Therefore, the stress is concentrated on each fixed portion when the case falls vertically, and there is a risk that a sterilization bag in the vicinity of the fixed portion may be damaged. Such a problem is not caused in the gap layer of the present invention, and a gap is ensured reliably during electron beam sterilization and the shock resistance in the upper and lower directions is also excellent.

Regarding the gap layer, from the viewpoint of shock resistance particularly in the vertical direction, the ratio of the thickness ($L_5$) of the gap layer between two body fluid treatment device layers and the thickness ($L_2+L_5+L_2$) between two body fluid treatment device layers including the gap layer ($L_5$) is preferably 0.01 or more and 1.20 or less. When the ratio is 0.01 or less, the damage to the sterilization bag and the damage to the product become remarkable, and the safety as the product cannot be ensured. The ratio is more preferably 0.05 or more. On the other hand, when the ratio is 1.20 or more, further effects cannot be obtained, and the volume occupied by the gap layer increases more than necessary, which reduces irradiation and transportation/transfer efficiencies. The ratio is more preferably 1.00 or less.

$$\text{Ratio of gap layer thickness} = \frac{\text{Thickness of gap layer between two body fluid treatment device layer } (L_5) \text{ (mm)}}{\text{Thickness of two body fluid treatment device layers including gap layer } (L_2 + L_5 + L_2) \text{ (mm)}} \quad (6)$$

In the present invention, it is more preferred that the average thickness of the gap layer be 10 mm or more and 100 mm or less.

Figure 3:
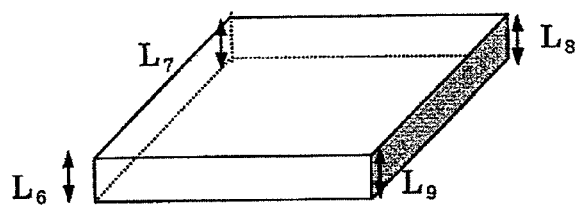
FIG. 3 is a schematic view illustrating positions for measuring the average thickness of the gap layer.

The average thickness as used herein is obtained by measuring thicknesses ($L_6$ to $L_9$) at four corners of the gap layer and averaging the thicknesses, as illustrated in FIG. 3. When the average thickness of the gap layer is smaller than 10 mm, the volume of the gap layer becomes small and the density in the case increases, with the results that the permeability of an electron beam is weakened and an absorbed dose distribution in one product increases. The average thickness is more preferably 20 mm or more, and particularly preferably 30 mm or more. On the contrary, even if the average thickness is set to be more than 100 mm, further effects cannot be obtained, and the volume occupied by the gap layer merely increases more than necessary. That is, compared with the case where the same numbers of devices are packaged, the case size becomes larger, or compared with the case where the devices are packaged in the same case, the number of the housed devices becomes little. Therefore, the dose of irradiation at a time is limited, and the irradiation efficiency is reduced. Further, the efficiency for transfer or storage is reduced. The average thickness is more preferably 85 mm or less, and particularly preferably 70 mm or less.

The stack structure as used herein refers to a structure in which one gap layer with a specified density described above is sandwiched between two body fluid treatment device layers with a specified density described above. For suppressing an absorbed dose distribution, it is necessary that each layer be housed in an electron beam-permeable case as a said stack structure and be subjected to electron beam sterilization.

FIGS. 9(a) to 9(j) illustrate embodiments in which a stack structure is housed in an electron beam-permeable case, and the embodiment illustrated in FIG. 9(a) is a basic configuration of the stack structure. The embodiments illustrated in FIGS. 9(c) to 9(j) illustrate further embodiments including the basic configuration, and any of them falls within the scope of the present invention. In the figures, the respective arranged cylinders correspond to body fluid treatment devices. The number thereof is not particularly limited.

As illustrated in FIG. 9(b) or 9(g), in body fluid treatment device layers opposed to each other via a gap layer, the fluid body treatment devices in the respective body fluid treatment device layers may be arranged in a zigzag manner in a circular cross-sectional direction. As illustrated in FIG. 9(d), 9(f), 9(i), or 9(j), in one body fluid treatment device layer, the body fluid treatment devices in adjacent rows may be arranged in a zigzag manner in a circular cross-sectional direction. In particular, it is preferred that the body fluid treatment device layers be arranged in two rows and in a zigzag manner, because the case size of a package may be made as small as possible while suppressing an absorbed dose distribution.

One or more stack structures may also be housed in a case as illustrated in FIG. 9(g). Further, as illustrated in FIG. 9(e) or 9(h), another gap layer is stacked on at least one of the body fluid treatment device layers, and a body fluid treatment device layer may also be stacked on the gap layer and housed in a case. In this case, it is necessary that any of either the gap layer or the body fluid treatment device layer to be stacked additionally be set to fall within the same density range as that of the stack structure. Further, as illustrated in FIGS. 9(c), 9(d), 9(f), 9(i) and 9(j), the body fluid treatment devices may be arranged in two rows in the body fluid treatment device layer. In the case of two rows, the body fluid treatment devices in the raw far from one gap layer needs to be in contact with a case surface, or to be in contact with another gap layer. In those embodiments, the number of devices housed in the package may preferably be held to a large extent while suppressing the absorbed dose distribution.

In the present invention, in order to further optimize the above stack structure, the shape of the body fluid treatment device layer may be devised. More specifically, it is preferred to use a body fluid treatment device package unit in which body fluid treatment devices are fixed substantially in parallel to each other in an axis direction on a rectangular electron beam-permeable tray, and are arranged in a row in a circular cross-sectional direction, and in which at least on a part of one side or adjacent two sides of the tray an obstacle capable of protruding in a perpendicular direction with respect to a horizontal surface of the tray is provided, and on a side opposed to the obstacle a cutout with a thickness equal to or larger than that of the obstacle is provided.

The rectangular electron beam-permeable tray refers to a square or rectangular horizontal plate body, and on one surface thereof a holding portion is provided, which fixes a plurality of body fluid treatment devices substantially in parallel to each other in the axis direction and arranges the body fluid treatment devices in a row in the circular cross-sectional direction thereof. Four corners may have R (roundness) from the viewpoint of the housing capability in a package case. It is not necessary to particularly limit the shape of the holding portion and the holding mechanism. However, for example, a form provided with a V-shaped or U-shaped dent commonly used in a package of a hemodialyzer and the like may be used. When such holding portions are provided on both sides of a tray, the body fluid treatment devices may be fixed to predetermined positions on the tray in the vicinity of both ends.

The tray should be the one which holds a horizontal shape withstanding the total weight even when a plurality of body fluid treatment devices are fixed in the manner described above. As long as the tray may hold a horizontal shape, a part of the surface of the tray may be provided with a cutout or a hole, or may have a lattice shape or a line shape. Further, as an embodiment in which a large cutout is provided on a tray surface so as to eliminate the tray surface to the utmost, an embodiment in which a tray is provided with a rectangular form having a holding portion of a body fluid treatment device and an obstacle capable of protruding upward from one or two sides of the form also falls within the tray according to the present invention.

For example, a tray may be formed of a board, a cardboard, a resin plate, a foam resin plate, or a material obtained by combining them arbitrarily or subjecting them to shaping for reinforcement. Further, if the tray is formed of paper, a pulp mold may also be used, and if the tray is formed of a resin plate, a tray having an uneven portion (convexo-concave portion) to serve as a holding portion or the like subjected to press working may be used. It should be noted that, each package is irradiated with an electron beam, and hence the tray as well as the package case needs to be electron beam-permeable. There is no particular limit as long as the electron beam permeability is at a negligible level compared with that of the body fluid treatment device, and a cardboard is preferred from the viewpoint of electron beam permeability, moldability and a cost, and the cardboard has less problem as a waste.

As described above, when a tray with body fluid treatment devices fixed thereto is housed in a case, it is particularly effective to arrange the respective body fluid treatment devices in a zigzag manner in a circular cross-sectional direction between the adjacent trays, for reducing irradiation non-uniformity of an electron beam. In order to achieve this arrangement state without mistakes during the packaging step in a production line, or in order to find a stacking error easily and exactly before the completion of packaging even if an operation is forced to be proceeded in a wrong state, it is necessary to provide an obstacle capable of protruding in a perpendicular direction to the horizontal surface of the tray to at least a part of one side or adjacent two sides of the tray to which body fluid treatment devices are fixed. This is described with reference to the drawings as follows.

Figure 5:
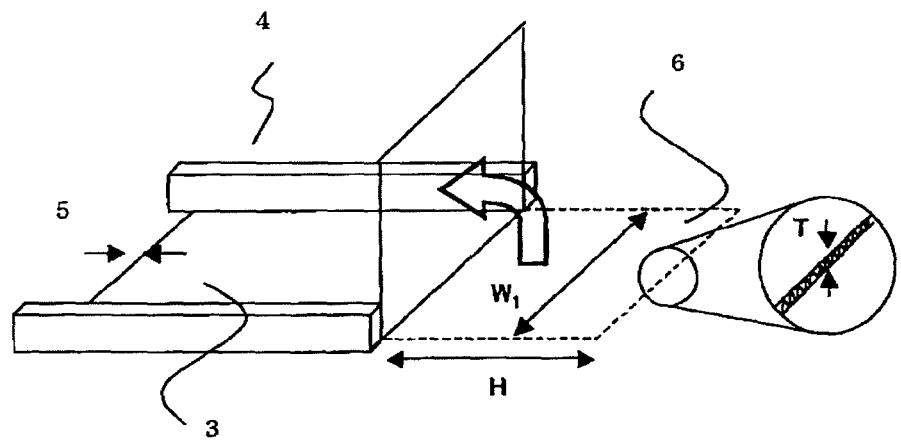
FIG. 5(a) is a schematic view illustrating a tray having an obstacle capable of protruding in a perpendicular direction at one side of the tray.
FIG. 5(b) is a schematic view illustrating the tray having obstacles capable of protruding in a perpendicular direction at two sides of the tray.
Figure 5:
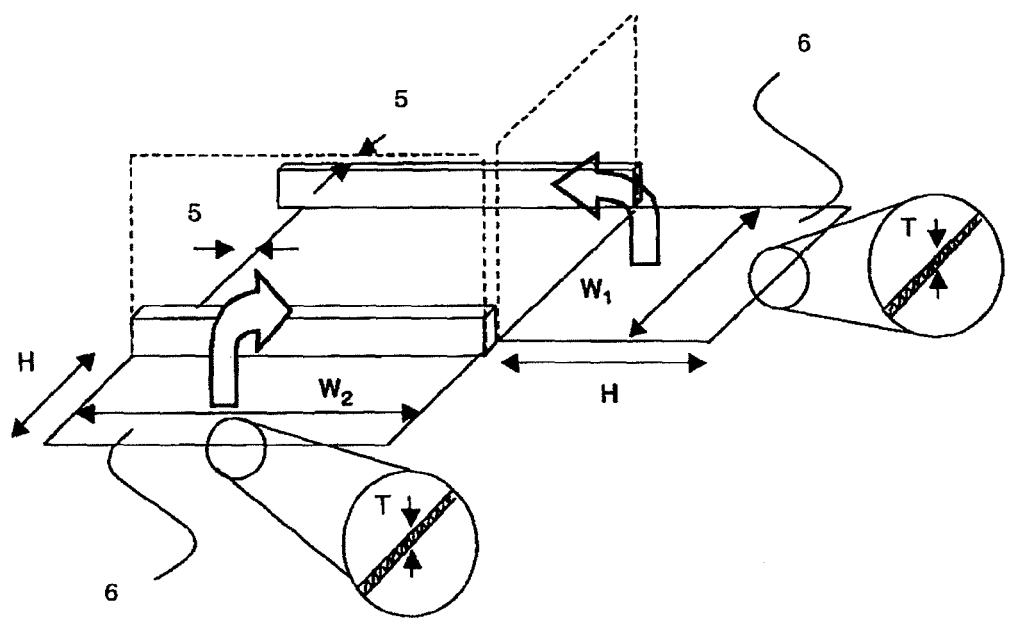

FIG. 5 illustrates an example of a package unit 4 in which an obstacle 6 is provided on a tray 3. FIG. 5(a) illustrates an embodiment in which the obstacle 6 capable of protruding in a perpendicular direction to the horizontal surface of the tray 3 is provided at one side of the tray 3 to which body fluid treatment devices are fixed, and FIG. 5(*b*) illustrates an embodiment in which the obstacles 6 are provided at two sides of the tray adjacent to each other.

Figure 6:
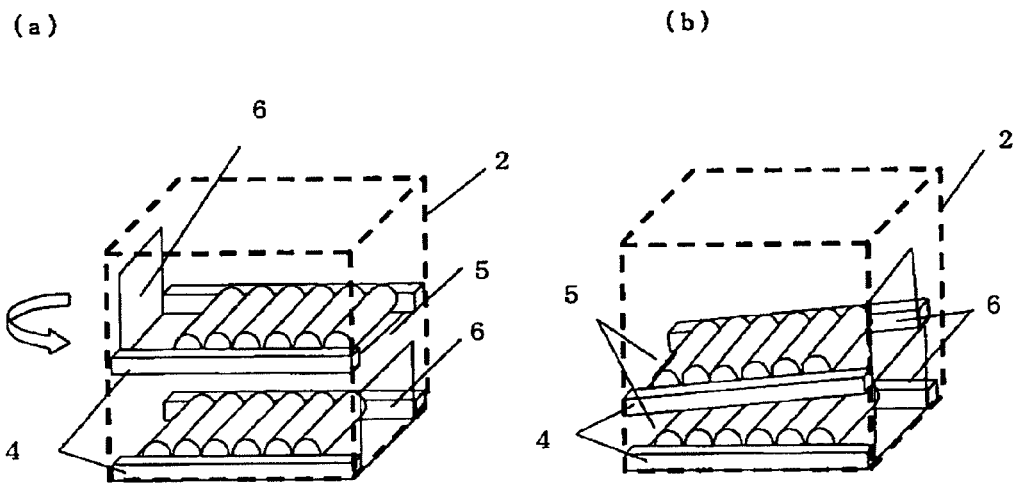
FIG. 6(a) is a schematic view illustrating a method capable of performing horizontal stacking smoothly.
FIG. 6(b) is a schematic view illustrating a method with which horizontal stacking cannot be performed smoothly.

The obstacle 6 refers to a structure that hinders the horizontal stacking when the package units 4 are housed and stacked in a packaging case. Specifically, the obstacle 6 is a structure that hinders a subsequent package unit 4 from being horizontal when the subsequent package unit is stacked just on a certain package unit. Further, the obstacle 6 is also a structure that allows one surface of the packaging case, which is to be planar originally, to swell abnormally, and hinders the sealing of an upper cover. As illustrated in FIGS. 5 and 6, the obstacle 6 being capable of protruding in a perpendicular direction to the horizontal surface of the tray 3 refers to the following state: the obstacle 6 is substantially along the horizontal surface of a tray before a package unit is housed in a packaging case, and the obstacle 6 rises and protrudes perpendicularly to the horizontal surface of the tray in a period from a time when the package unit starts being housed in the packaging case to a time when the package unit has been housed completely.

Generally, when package units are sequentially stacked in a packaging case, in order to prevent body fluid treatment devices on a tray from falling, the package units are allowed to sink to a bottom portion gently while substantially keeping a horizontal state. On the other hand, during transportation, in order to prevent each package unit in the case from moving around freely, a large gap is not provided between the package unit and the inner wall of the packaging case. At this time, in the package unit provided with the above-mentioned obstacle, the obstacle abuts on the inner wall of the packaging case, which is close to the obstacle. As a result, the package unit sinks with the obstacle rising in a perpendicular direction (opposite direction to a sinking direction) with respect to the horizontal surface of the tray and stops with the obstacle protruding upward. If the package unit is allowed to sink with the obstacle facing downward for some factor, the obstacle abuts on the bottom surface of the packaging case to prevent sinking. As a result, it becomes difficult to keep the package unit horizontally in the bottom portion of the case. Thus, it is detected immediately that the package unit has not been housed properly.

FIG. 6 illustrates an example of a stacked state of the package units 4 in the packaging case 2. As illustrated in FIG. 6(*a*), when a subsequent package unit 4 is stacked after the package unit 4 in the first layer is housed property in the bottom portion of the packaging case 2, if the package unit 4 to be stacked is inverted by 180° in the horizontal direction with respect to the package unit 4 placed immediately below, the package unit 4 may be stacked smoothly and horizontally without abutting on the obstacle 6 in the lower stage. This also applies similarly to the case where the package units 4 are sequentially stacked as the third layer, fourth layer and so on. However, as illustrated in FIG. 6(*b*), when an attempt is made to stack the subsequent package unit 4 in the same direction without inverting the package unit 4, the obstacle 6 in the lower stage abuts on the bottom surface of the subsequent package unit 4 to hinder sinking, with the result that the package unit 4 cannot be stacked smoothly and horizontally any more. At this time, if the package unit 4 is forcedly stacked with an excessive force, the package unit 4 may be stacked diagonally. Otherwise the obstacles 6 overlap at the same position. Consequently, a part of the packaging case 2 swells abnormally, and hence, it is very easily detected that the package unit 4 is not stacked properly.

In the present invention, as the shape of the obstacle a cylindrical shape, a triangular prism, a rectangular prism, a plate shape, or the like is considered. However, the present invention is not limited thereto, as long as the function as the obstacle is fulfilled. Such an obstacle may be provided to at least a part of one side of a tray or two adjacent sides, or may be provided at the whole sides. Considering that a tray is delivered as one package member, a package unit including an obstacle is preferably in a plane shape as a whole from the viewpoint of a packaging capability during transportation. That is, as illustrated in FIGS. 5(*a*), 5(*b*), and 6(*a*), it is preferred that the obstacle has a horizontal plate shape along the surface of the tray 3 at a time of delivery of a package unit, and rises easily at a time of being housed in the packaging case. In addition, it is more preferred that the obstacle is capable of folding inward (on an acute angle side) from the perpendicularly rising state. The reason is as follows: though there is no problem in the case where there is spatial room between the stacked uppermost stage and the cover in the packaging case, it is difficult to close the packaging case if there is no such spatial room. If the obstacle may be capable of folding inward, even in the case where the obstacle 6 in the uppermost stage of the package protrudes out of the uppermost portion of the case, the obstacle 6 may be folded integrally with the cover portion to be closed.

In order to enable such perpendicular rising and further inward holding, a movable portion may be provided between the tray and the obstacle, i.e., in a side portion. Examples of the movable portion include a fold, a thin portion, and a hinge. Though there is no particular limit to an obstacle, an obstacle, which cannot maintain a perpendicular state when housing in a packaging case and falls inward immediately, is hard to function as an obstacle. Therefore, the obstacle preferably has mobility to such a degree that the obstacle may be folded arbitrarily by a human hand.

Unless the flatness as a member at the time of delivery is particularly concerned, the obstacle 6 may protrude in a perpendicular direction with respect to the tray 3 at the beginning irrespective of the shape. In this case, the movable portion is not particularly necessary at a side of a tray on which a plate-shaped body is provided. In the embodiment, the effect of preventing a stacking error, which is required in the present invention, may be obtained without fail. Considering the handleability as such one member and the functionality during use, as a specific example of the obstacle, a plate-shaped body extending continuously from one side of a tray or two adjacent sides thereof is preferred because it is structurally simplest.

In FIG. 5, the width (symbols: $W_1$, $W_2$) and the thickness (symbol: T) of the plate-shaped obstacle 6 are not limited as long as the function as the obstacle is fulfilled. However, when the width is too small, the strength becomes weak. Therefore, when an upper package unit is stacked in a wrong direction, the obstacle is easily crushed, which increases a risk that a stacking error cannot be detected precisely. Thus, it is preferred that the width (symbols: $W_1$, $W_2$) of the plate-shaped obstacle be 30 mm or more and equal to or less than the width of the side of the tray at which the obstacle is provided. The thickness T may be the same as that of the tray in the case where the obstacle is a plate-shaped body extending from one side or two adjacent sides of the tray, and if the thickness T is 3 mm or more and 10 mm or less, the obstacle functions sufficiently. In the case where the thickness is small, the tip end of the plate-shaped obstacle is folded in valley fold or mountain fold, whereby the thickness to be an obstacle to the sinking of the package unit to be stacked from above may be increased, which may further enhance the effect of preventing a stacking error. Regarding the height (symbol: H) of the obstacle 6, it is important that the obstacle may be visually inspected in the case where a package unit is stacked in a wrong way, and hence, the height is preferably 100 mm or more, and more preferably 150 mm or more. On the other hand, when the height is too high, the fear increases that the obstacle exceeds the size of a rectangular packaging case when the obstacle in the uppermost stage is folded. Therefore, it is preferred that the height be set to be equal to or less than the size of an opening of a case.

On the other hand, in the tray 3, it is required that a side facing the obstacle 6 is provided with a gap for allowing a package unit to be housed smoothly, while avoiding an obstacle in the lower stage, when the package unit is stacked properly, i.e., a cutout 5 with a thickness equal to or more than that of the obstacle. The shape of the cutout 5 may be the one which does not abut on the obstacle in the lower stage. When the cutout 5 is enlarged more than necessary, the fixing capability of the package unit in the packaging case is degraded, and hence, it is preferred that the shape of the cutout 5 is complementary to the shape and thickness (symbol: T) of the obstacle 6.

In a body fluid treatment device package of the present invention in which package units are stacked in a plurality of stages in a packaging case, an obstacle of the package unit protrudes perpendicularly to the horizontal surface of the tray. However, in the package unit placed immediately above the stacked package unit, the obstacle of the package unit placed immediately below protrudes through the cutout portion, and hence, a horizontal state is kept. Further, package units are engaged with each other complementarily as described above, and consequently, the vibration and movement of the package units may be suppressed in the packaging case, which also contributes to the further stabilization of the packaged state.

Figure 7:
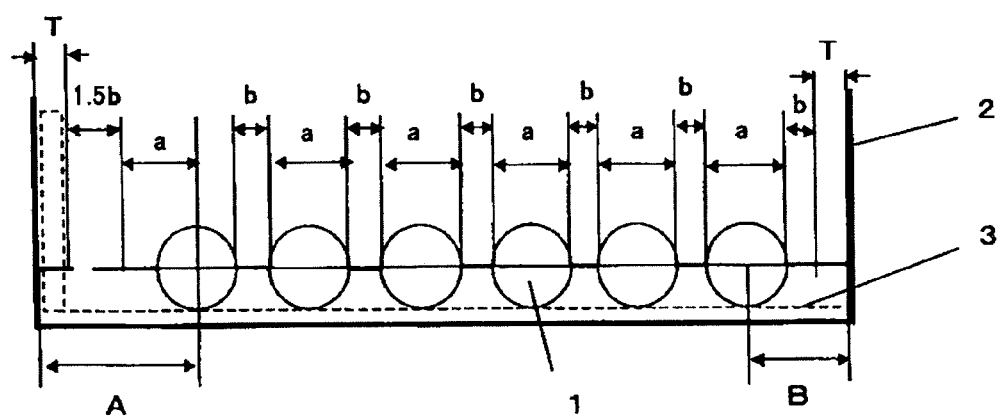
FIG. 7 is a schematic view illustrating a positional relationship for setting body fluid treatment devices on the tray. (circular cross-sections adjacent to each other have an equal interval.)

FIG. 7 illustrates an example of the arrangement of body fluid treatment devices on a package unit in detail. As illustrated in FIG. 7, if a distance A from the center of a circular cross-section of a body fluid treatment device at one end to the inner wall of one side at which an obstacle is provided in a tray and a distance B from the center of a circular cross-section of a body fluid treatment device at the other end to the inner wall of a side facing the obstacle in the tray have a relationship of A≠B, as long as there is no large gap between the package units and the inner wall of the packaging case, and the package units are inverted and stacked one by one, the respective body fluid treatment devices in the packaging cases are not lined up every one stage without being stacked so as to be aligned in the same line in a vertical direction. That is, a zigzag arrangement is achieved.

Herein, when the diameter of a circular cross-section of a body fluid treatment device is represented by "a", the arrangement interval of the circular cross-sections of the body fluid treatment devices is represented by "b", the thickness of the obstacle is represented by "T", and a constant is represented by "α", the distance "A" from the center of a circular cross-section of a body fluid treatment device at one end of the tray to the inner wall of one side at which an obstacle is provided in the tray should be A=a+αb+T, and the distance "B" from the center of a circular cross-section of a body fluid treatment device at the other end to the inner wall of a side facing the obstacle in the tray should be B=0.5a+b+T.

Here, the diameter "a" of the circular cross-section of the body fluid treatment device is preferably 30 mm to 80 mm, the arrangement interval "b" of the body fluid treatment devices is preferably 1 mm to 80 mm, the thickness "T" of the obstacle is preferably 3 mm to 10 mm, and the constant "α" is preferably 1.0 to 2.0, and more preferably 1.5. Those distances are appropriately adjusted by the location of a holding portion of the body fluid treatment devices provided on the tray, for example, the location of a V-cut.

An electron beam-permeable rectangular packaging case as used herein refers to a cubic or rectangular external container housing the above-mentioned package units in a stacked state. The material for the packaging case is desirably a cardboard or a plastic sheet, considering the ease of packaging, the cost thereof, and further the strength thereof. However, there is no particular limit, as long as the material has an electron beam permeability of a negligible level compared with that of the body fluid treatment device. However, the following should be noted. In order to prevent the package units in the packaging case from moving arbitrarily in the horizontal direction during transportation, an average value of a gap between each side of the sides at both ends of the tray and the inner wall of the case close to each side of the sides at both ends of the tray (hereinafter, referred to as average gap) is preferably small. The average gap should be generally about 1 to 2 mm, and a gap at such a degree is more preferred for preventing a stacking error because there is no fear that a package unit is stacked forcedly while an obstacle in the present invention facing in the same direction as is.

If a gap between body fluid treatment devices is provided, that is, a sufficiently large gap is provided on the periphery of each body fluid treatment device, it is considered that the fluctuation in transmittance of an electron beam is alleviated to some extent, in terms of the property of an electron beam. However, in the case where a plurality of body fluid treatment devices are packaged in an electron beam-permeable case and sterilized at a time, such a space remarkably increases a case size. On the other hand, the case size that may house body fluid treatment devices is determined to some extent due to the constraint in production steps and medical facilities.

An individual body fluid treatment device in a dry or semi-dry state has a small weight, and hence, there is a large advantage that a large number of such body fluid treatment devices may be housed in a case, sterilized, transported, stored, and easily handled in a medical facility by the case. Thus, the decrease in a packaging efficiency should be avoided. An electron beam sterilization method using the stack structure of the present invention exactly solves this problem. Though the detailed reason why the stack structure of the present invention may decrease an absorbed dose distribution has not been sufficiently clarified, it is conjectured that this phenomenon results from the balance between the maintenance of the permeability of an electron beam to be irradiated and the appropriate scattering.

The packaging efficiency as used herein refers to how many body fluid treatment devices are contained in a unit volume of an electron beam-permeable case, and is represented by the following Equation (7).

$$\text{Packaging efficiency (piece/cm}^3) = \frac{\text{Total number of body fluid treatment devices contained in case (piece)}}{\text{Volume of electron beam-permeable case (cm}^3)} \quad (7)$$

In terms of the transportability, handleability, and storagability, the packaging efficiency is preferably 3.0E-04 or more. It is not preferred that the packaging efficiency be lower than this range, because the number of body fluid treatment devices housed in one case becomes remarkably small, which is not practical.

The electron beam-permeable case as used herein refers to a cubic or rectangular external container housing at least one stack structure formed of a gap layer and body fluid treatment device layers. In the present invention, body fluid treatment device layers and gap layers are housed in a case so as to form a specified stack structure, and a plurality of body fluid treatment devices are sterilized with an electron beam at a time in this state, whereby sterilization is performed efficiently with a small absorbed dose distribution. The material for the electron beam-permeable case is desirably a cardboard or a plastic sheet, considering the ease of packaging, the cost thereof, and further the strength thereof. However, there is no particular limit, as long as the material has an electron beam permeability of a negligible level compared with that of the body fluid treatment device.

The electron beam sterilization method for a body fluid treatment device as used herein refers to the following method: body fluid treatment devices are packaged in sterilization bags and housed in an electron beam-permeable case as a stack structure, and thereafter, a plurality of body fluid treatment devices are housed and sterilized with an electron beam. The average irradiation dose of an electron beam irradiated to the body fluid treatment devices is preferably 5 to 50 kGy, more preferably 15 to 30 kGy, and particularly preferably 18 to 25 kGy.

Figure 9:
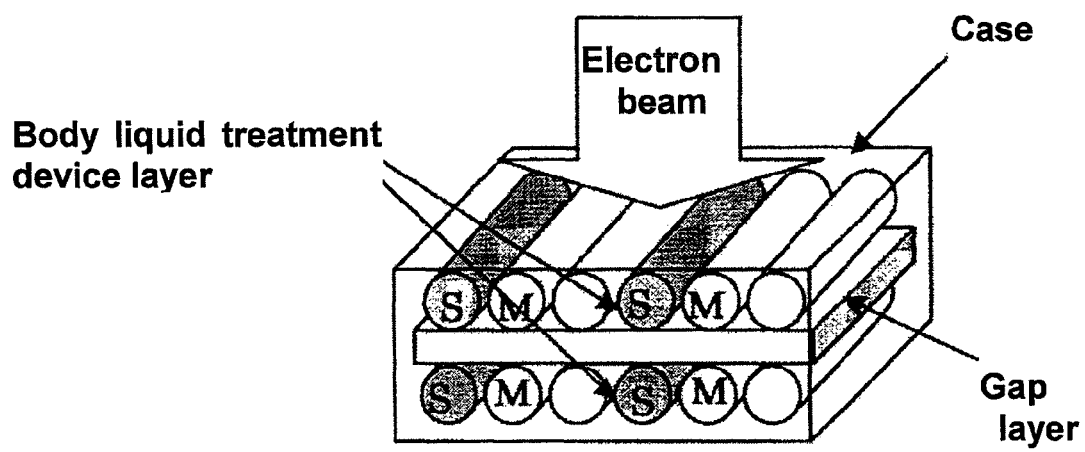
FIG. 9(a) is a schematic view illustrating a stack structure of members used in Example 1.
FIG. 9(b) is a schematic view illustrating a stack structure of members used in Example 2.
FIG. 9(c) is a schematic view illustrating a stack structure of members used in Example 3.
FIG. 9(d) is a schematic view illustrating a stack structure of members used in Example 4.
FIG. 9(e) is a schematic view illustrating a stack structure of members used in Example 5.
FIG. 9(f) is a schematic view illustrating a stack structure of members used in Example 6.
FIG. 9(g) is a schematic view illustrating a stack structure of members used in Example 7.
FIG. 9(h) is a schematic view illustrating a stack structure of a member used in Example 8.
FIG. 9(i) is a schematic view illustrating a stack structure of members used in Example 9.
FIG. 9(j) is a schematic view illustrating a stack structure of members used in Example 10.
FIG. 9(k) is a schematic view illustrating a stack structure of members used in Comparative Example 1.
FIG. 9(l) is a schematic view illustrating a stack structure of members used in Comparative Example 2.
FIG. 9(m) is a schematic view illustrating a stack structure of members used in Comparative Example 3.
FIG. 9(n) is a schematic view illustrating a stack structure of members used in Comparative Example 4.
FIG. 9(o) is a schematic view illustrating a stack structure of members used in Comparative Example 5.
FIG. 9(p) is a schematic view illustrating a stack structure of members used in Comparative Example 6.
FIG. 9(q) is a schematic view illustrating a stack structure of members used in Comparative Example 7.
FIG. 9(r) is a schematic view illustrating a stack structure of members used in Comparative Example 8.
Figure 9:
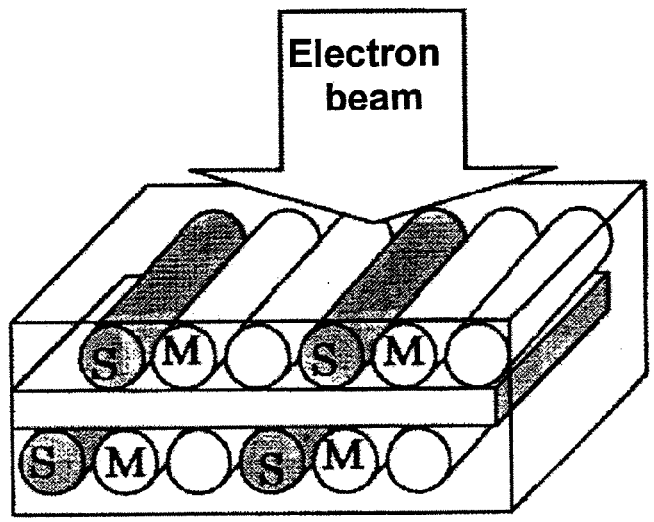
Figure 9:
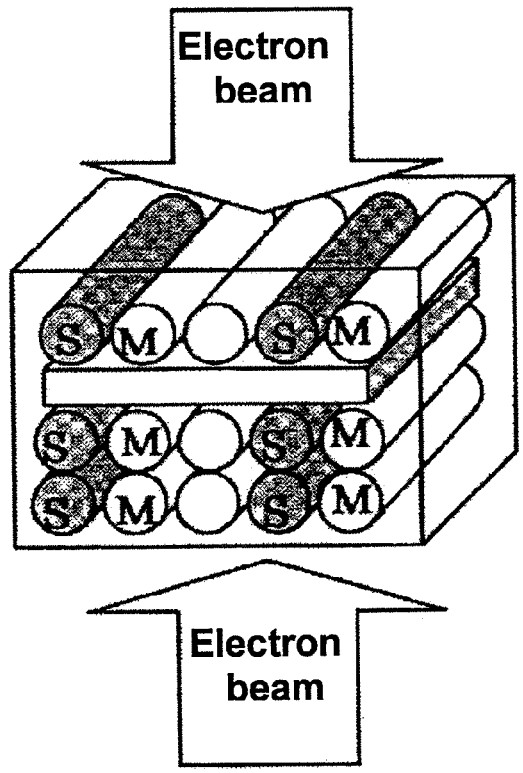
Figure 9:
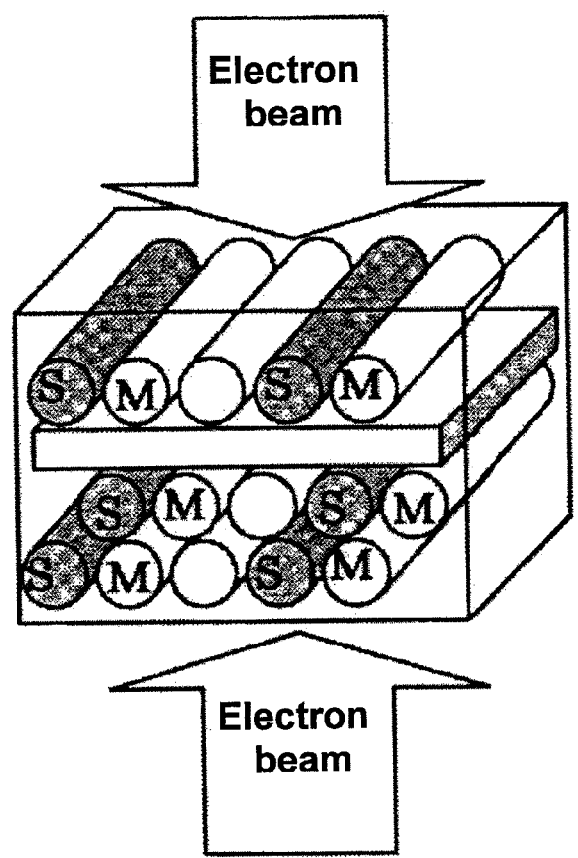
Figure 9:
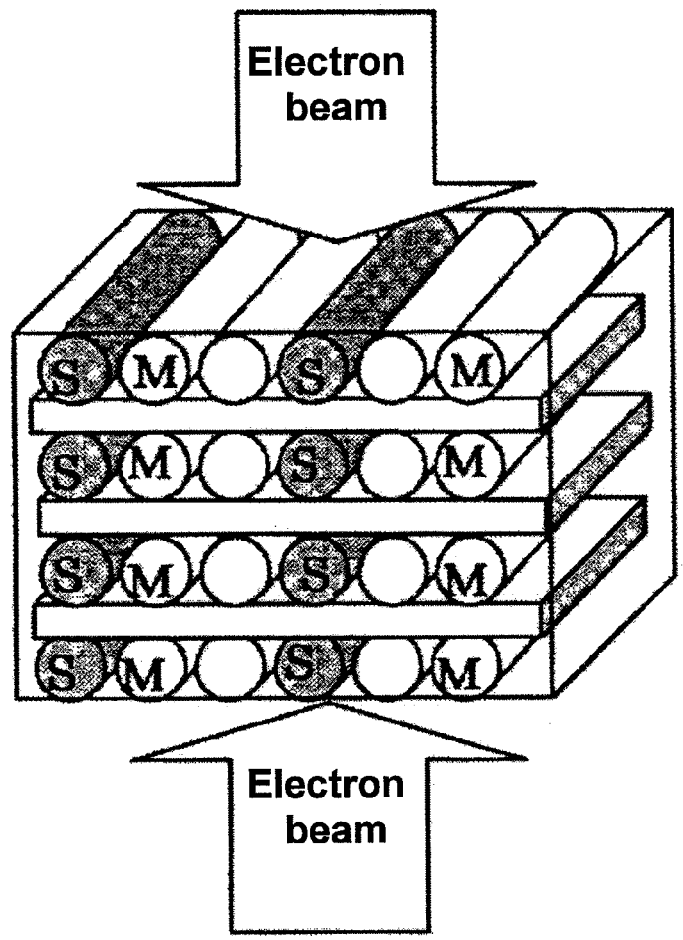
Figure 9:
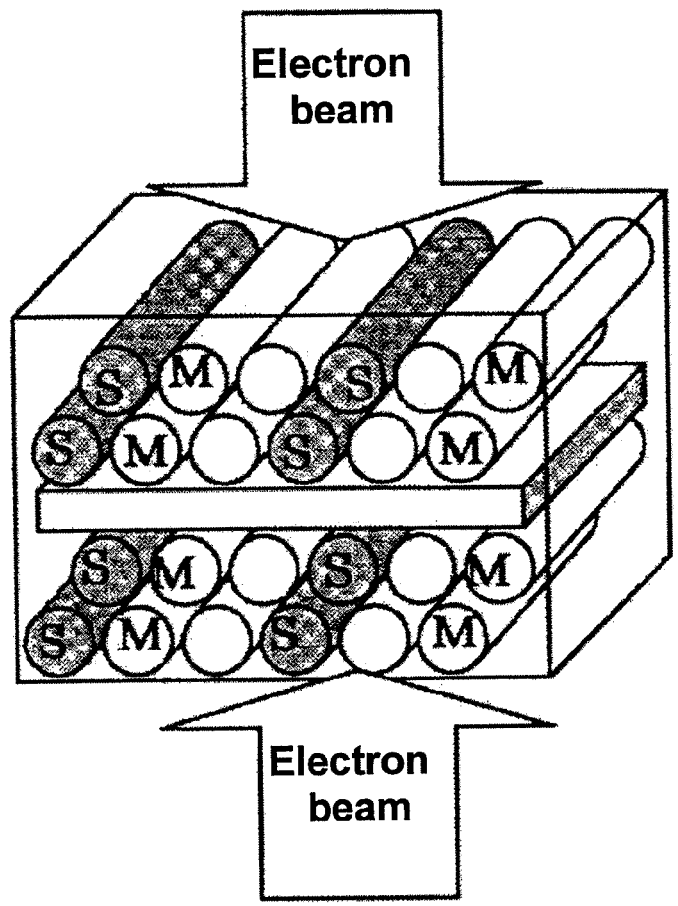
Figure 9:
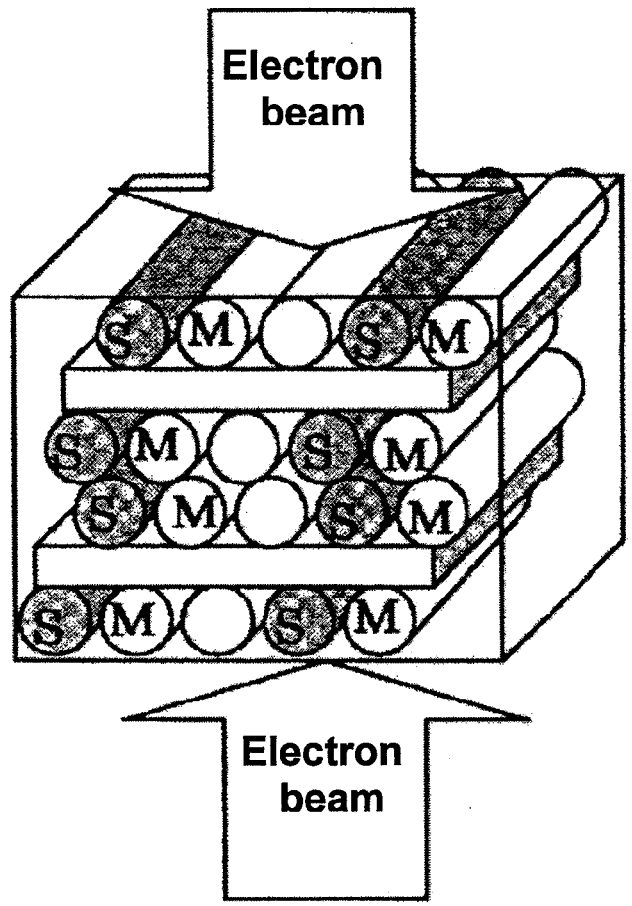
Figure 9:
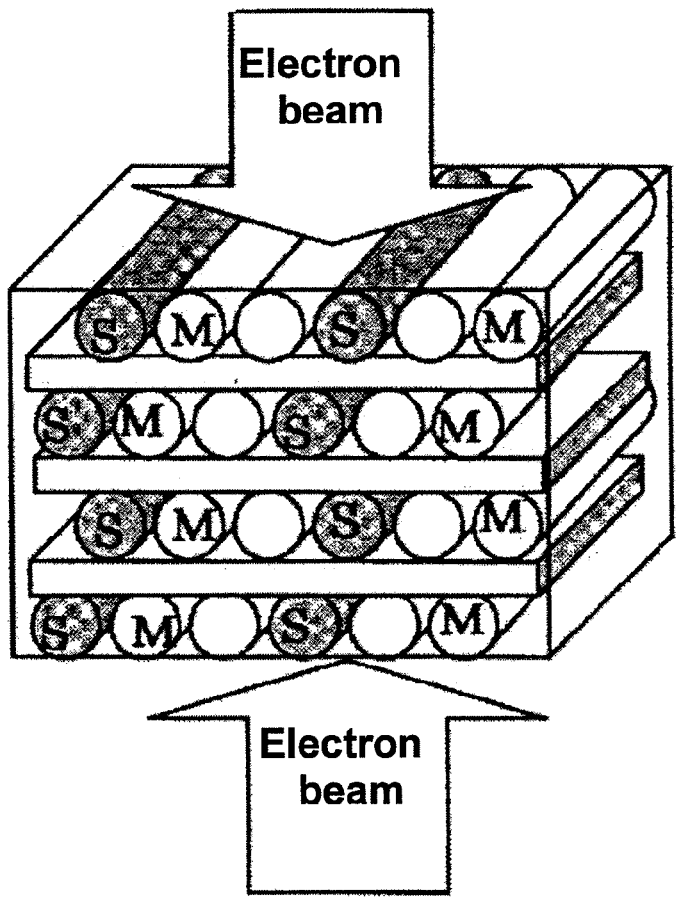
Figure 9:
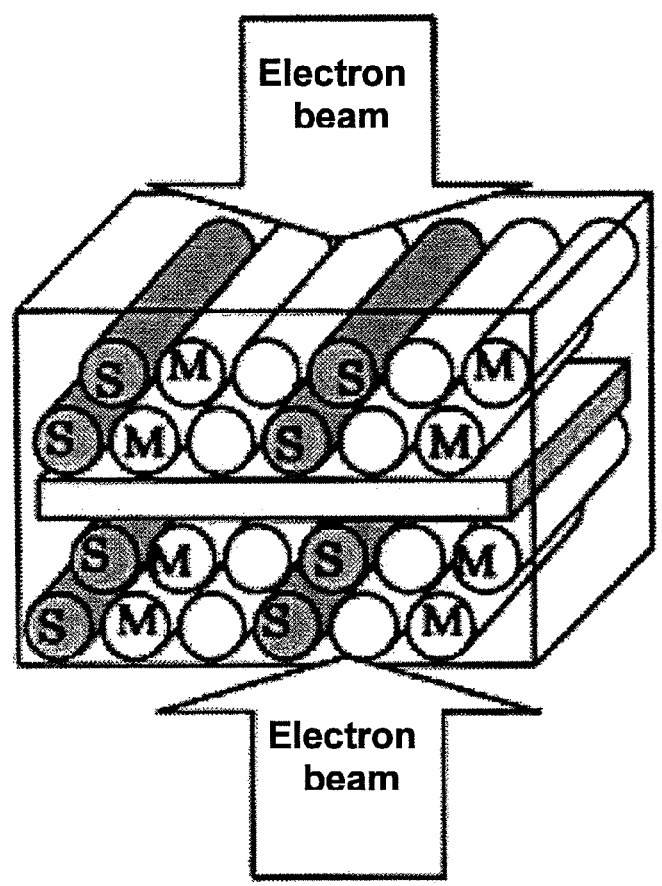
Figure 9:
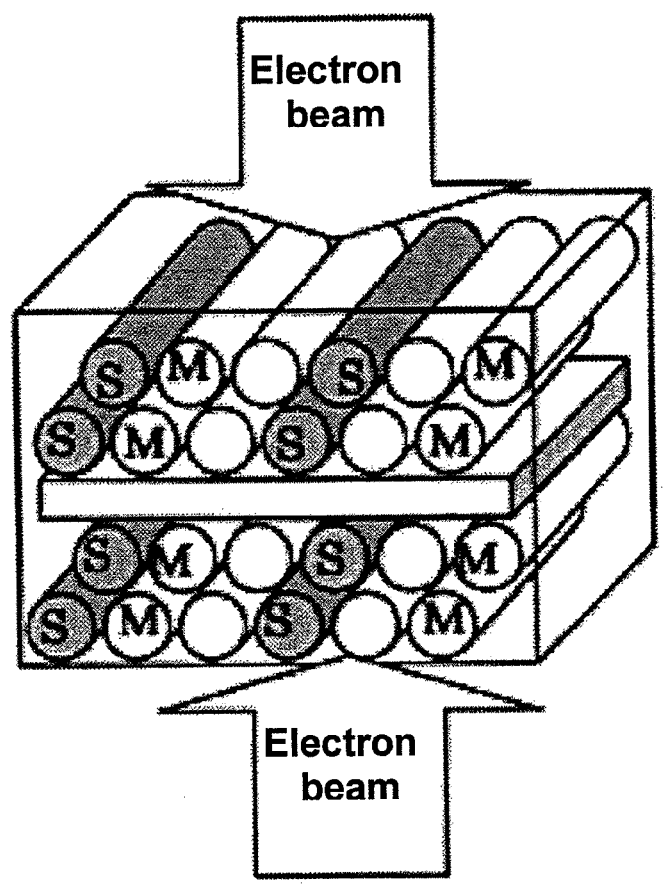
Figure 9:
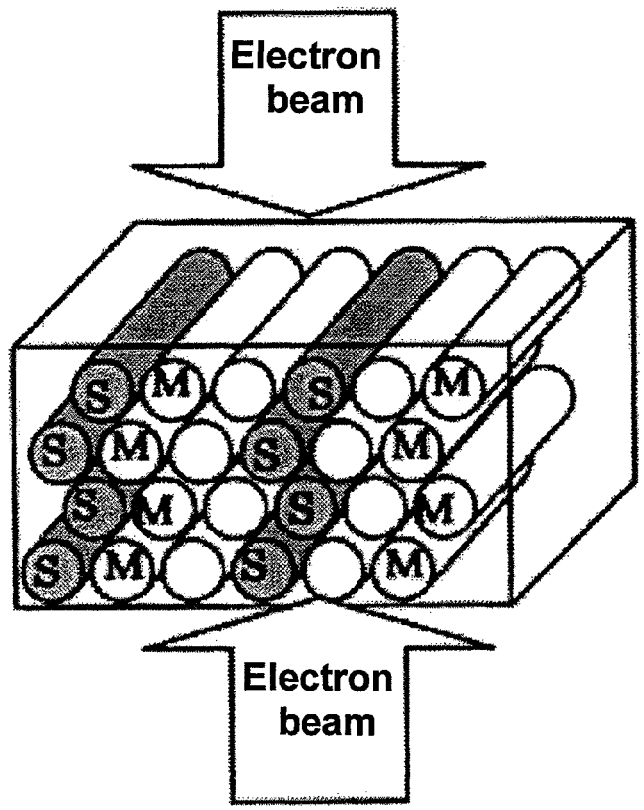
Figure 9:
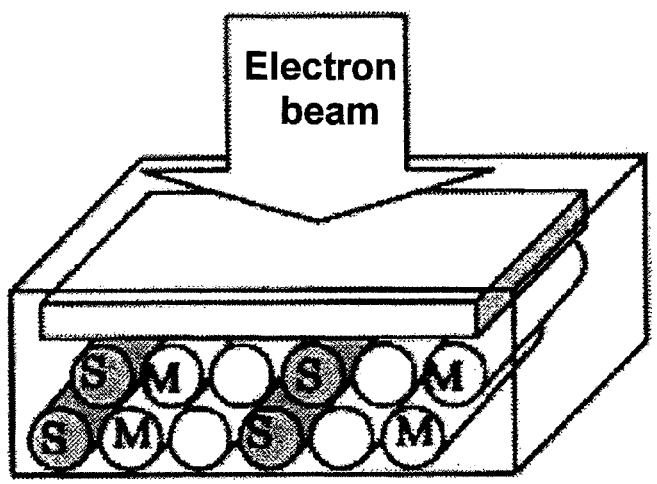
Figure 9:
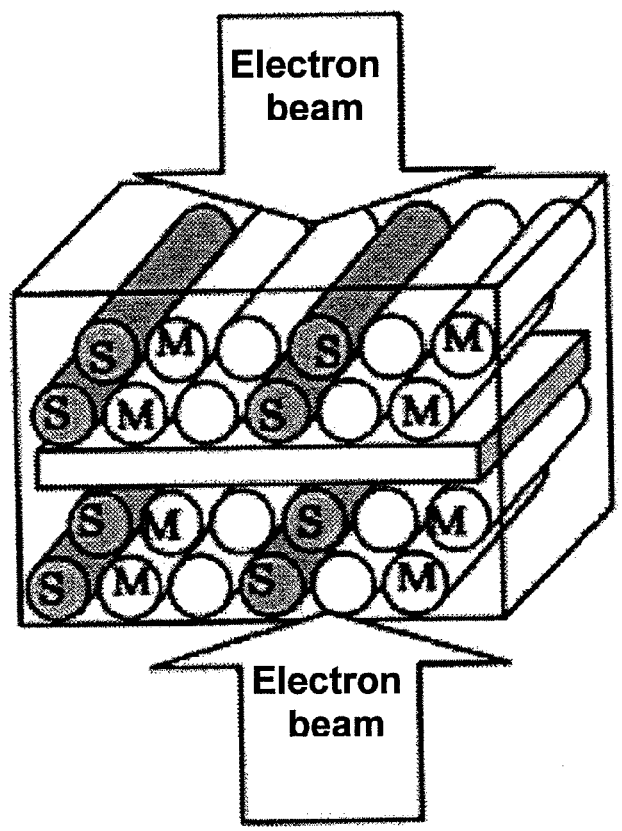
Figure 9:
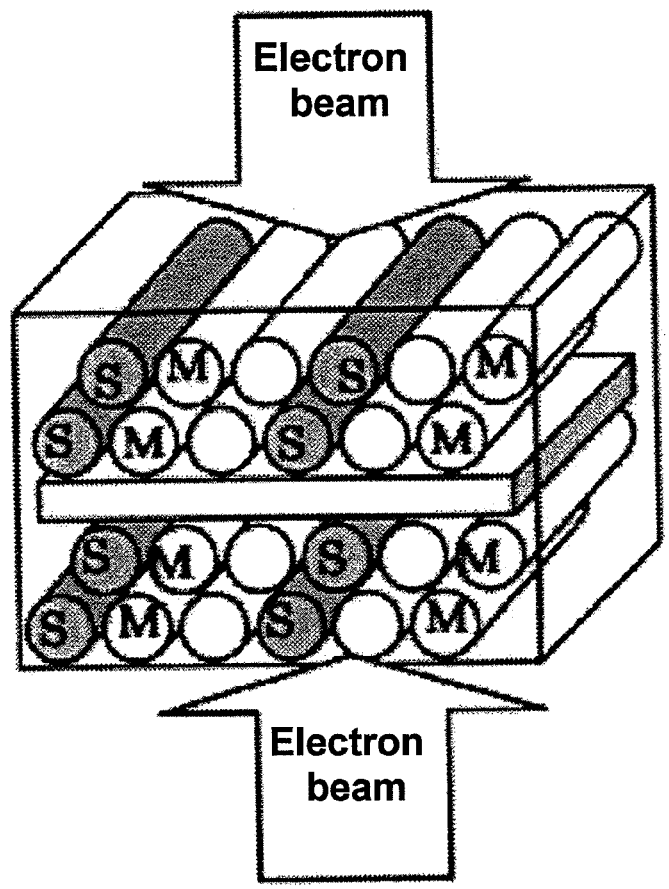
Figure 9:
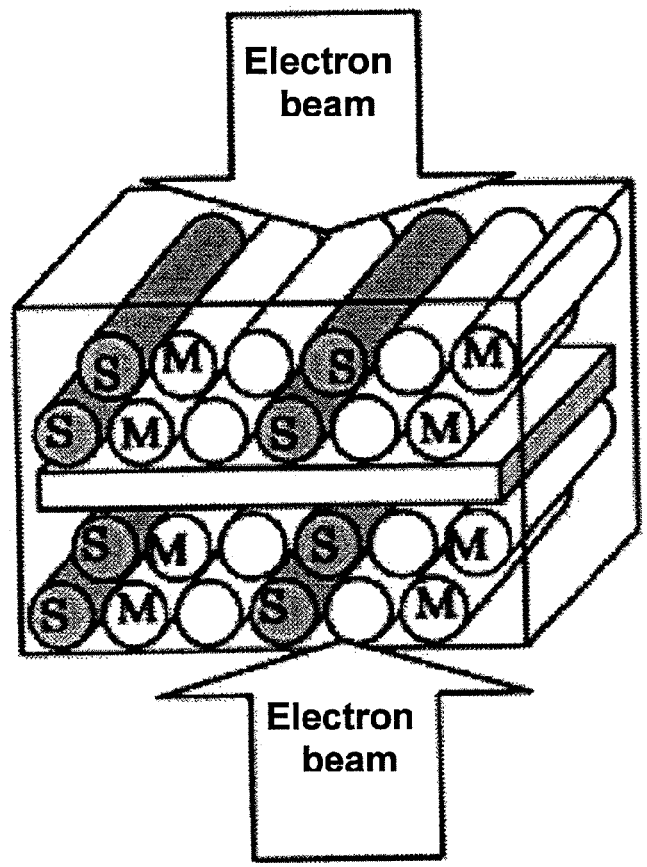
Figure 9:
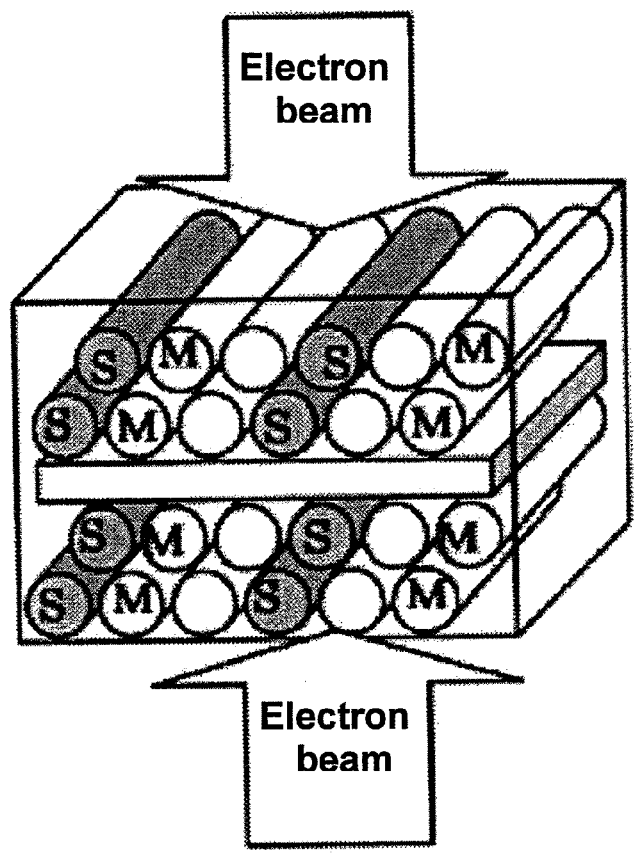
Figure 9:
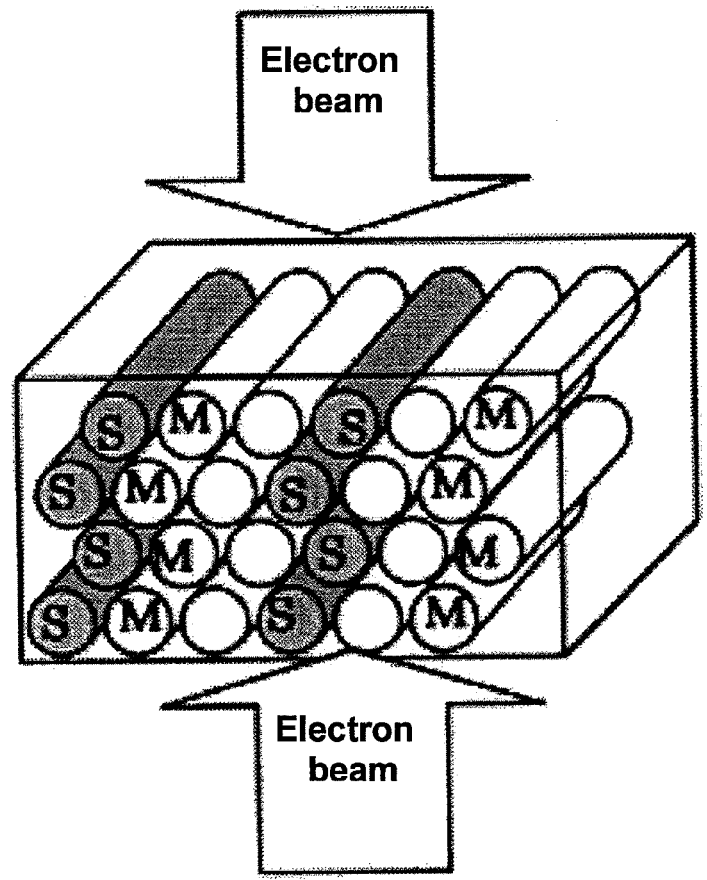
Figure 9:
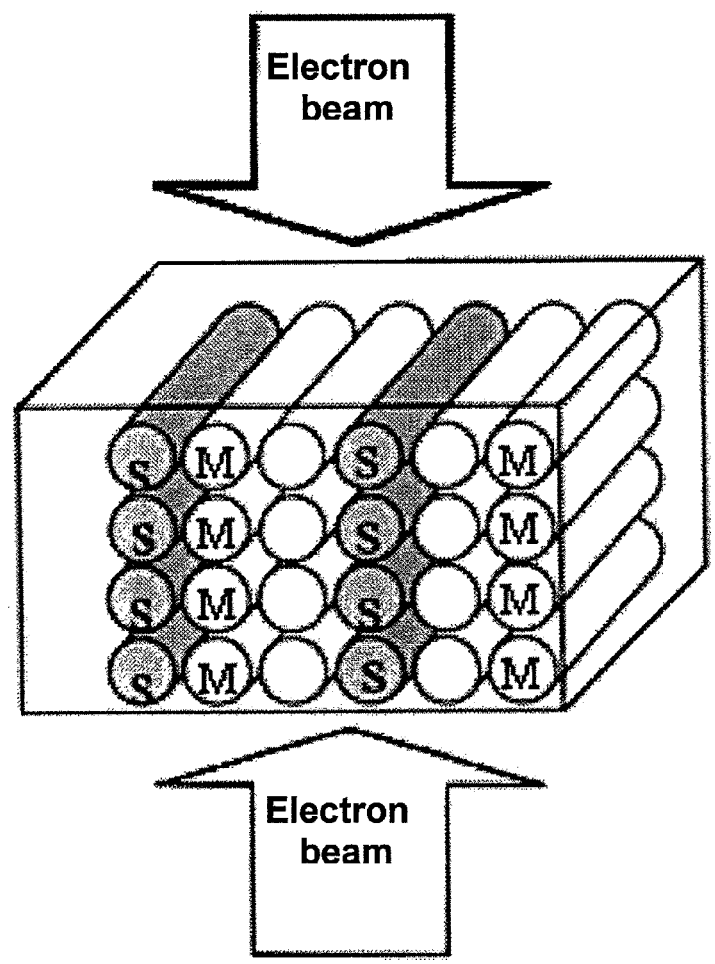

Regarding to an irradiation method for an electron beam, as illustrated in FIG. 9, an electron beam is irradiated to an electron beam-permeable case housing a stack structure of the present invention from a substantially perpendicular direction of the stack structure, or an electron beam may be irradiated to the stack structure from a substantially parallel direction. The present invention is not limited to any of them. At that time, two irradiations from two opposite directions of the electron beam-permeable case, i.e., the inversion irradiation is preferred for further decreasing an absorbed dose distribution.

EXAMPLES

Hereinafter, the present invention is described more specifically with reference to the examples, but the present invention is not limited to the following examples. First, various measurement methods used in the examples are described.

[Method of Measuring an Absorbed Dose Distribution]

An absorbed dose distribution was measured as an absorbed dose fluctuation among body fluid treatment devices, using a plurality of body fluid treatment devices for measuring an absorbed dose in which cellulose triacetate (CTA) dosimeter FTR-125 manufactured by Fuji Photo Film Co., Ltd. was embedded. The dosimeter has a sheet shape, and may be cut to various sizes and shapes to be fixed to an object to be irradiated. The dosimeter was measured using a previously calibrated calorimeter manufactured by RISO National Laboratory.

Figure 4:
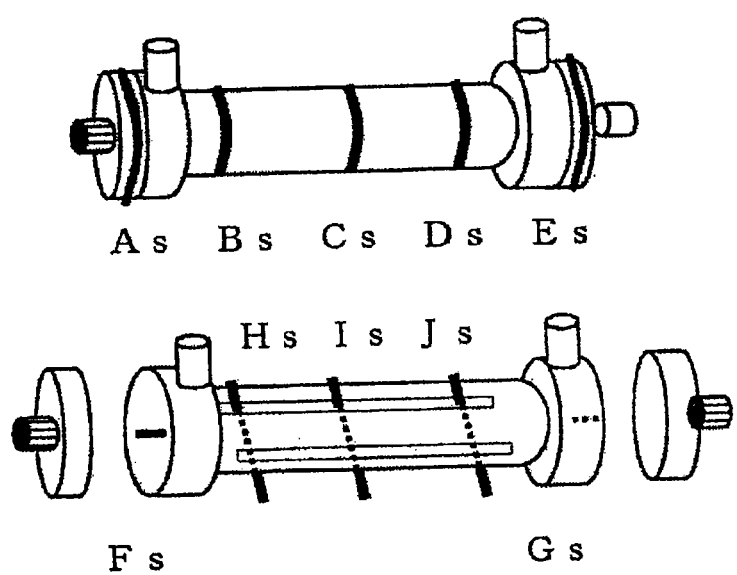
FIG. 4 is a schematic view illustrating positions for attaching dosimeters.

As illustrated in FIG. 4, the dosimeters were attached to 5 places (As to Es) in a state of being wound around the circumference of a body portion of a body fluid treatment device, attached to 2 places (Fs, Gs) in a state of being embedded in a potting agent, and attached to 3 places (Hs, Is, Js) in a state of being embedded in a separation material.

The body fluid treatment devices for measuring an absorbed dose were arranged in a case as indicated by a symbol "S" in FIGS. 9(a) to 9(r). Each absorbed dose was measured, and thereafter, a ratio of a maximum value to a minimum value was used as a maximum to minimum dose ratio.

[Evaluation of Material Deterioration]

Using a hollow fiber membrane type blood purification device composed of polysulfone and polyvinyl pyrolidone (hereinafter, abbreviated as "PVP") as a body fluid treatment device, an elution amount of PVP was used as an index for evaluating the material deterioration.

As indicated by a symbol "M" in FIGS. 9(a) to 9(r), the body fluid treatment devices for measuring the material deterioration arranged in a case were measured by the following method, and an average PVP elution amount was calculated.

The blood side and the dialysate side of the hollow fiber membrane type blood purification device are each washed with 1 liter or more of injection water (Japanese Pharmacopoeia) sufficiently. The liquid is sufficiently removed by injecting compressed air. Then, injection water (Japanese Pharmacopoeia) heated to 70° C. is circulated through the blood side at a rate of 200 ml/min for 1 hour in a state in which the dialysate side of the blood purification device is sealed. After 1 hour of circulation, the collected extract is filtered through a filter with a pore size of 0.45 μm. The PVP concentration in the filtrate is measured using an HPLC ("LC-10AD/SPD-10AV" manufactured by Shimadzu Corporation). The HPLC conditions are as follows;

Column: Shoudex Asahipak GF-710HQ,
Mobile phase: 50 mM NaCl aqueous solution,
Flow rate: 1.0 ml/min,
Temperature: 30° C.,
Detection: 220 nm, and
Injection: 50 μl.

[Vibration and Drop Test]

The body fluid treatment devices arranged in a case, as illustrated in FIG. 9, were subjected to a vertical vibration for 15 minutes with 15 Hz×0.5 G and for 45 minutes with 10 Hz×0.75 G in accordance with JIS Z 0232: Packaged freights-Method of vibration test in a packaged state. After that, the body fluid treatment devices were subjected to one corner, three edges, and six faces dropping from a drop height of 80 cm each, in accordance with JIS Z 0202: Method of drop test for packaged freight. Each body fluid treatment devices was taken out from the case, and all the devices were observed for the appearance and examined for a sterilization bag breakage and a hollow fiber membrane leakage.

A leakage test was performed as follows: one header of a body fluid treatment device sunk in water was sealed and the body fluid treatment device was pressurized (0.15 MPa) with compressed air from another header, and a leakage was determined when the generation of air bubbles from a hollow outside was recognized after 30 seconds.

[Measurement Method for Oxygen Concentration]

The oxygen concentration in the body fluid treatment device was measured before electron beam sterilization treatment using a trace oxygen analyzer ("RO-102 type" manufactured by Iijima Electronics Corporation) in a state in which the body fluid treatment device was sealed in a sterilization bag. During measurement, in order to prevent the inflow of air from outside of the sterilization bag, adhesive rubber ("adhesive rubber RG-1 type" manufactured by Iijima Electronics Corporation) was attached to the outside of the sterilization bag, an oxygen suction probe of a measurement device was speared through the adhesive rubber, and the concentration of oxygen in the sterilization bag was measured. A separation material had a gas permeability, and hence, the concentrations of oxygen inside and outside of the separation material in the sterilization bag were considered to be uniform.

Example 1

A bundle of about 16,000 hollow fiber polysulfone-PVP based dialysis membranes were set as a separation material in a cylindrical resin container having two inlet and outlet ports for a fluid in the vicinity of both ends, and the both ends were subjected to potting with a urethane resin. A glycerin aqueous solution was injected from the ends, and a remaining fluid was blown away with compressed air to adjust the liquid adhesion rate of the membranes to 200%. After that, headers having liquid inlet and outlet ports were attached to both ends to obtain a body fluid treatment device. The body fluid treatment device had a whole length of 335.2 mm, a minimum diameter (container body portion) of 46.9 mm, and a maximum diameter (header portion) of 59.0 mm. The body fluid treatment devices were sealed in sterilization bags made of nylon/polyethylene one by one. At this time, as a body fluid treatment device for measuring a dose distribution, a body fluid treatment device illustrated in FIG. 4 was also prepared.

Next, two body fluid treatment device layers were prepared, in which six body fluid treatment devices were arranged at equal intervals and substantially in parallel on a cardboard tray of $L_{13}$ 385 mm×$L_{14}$ 355 mm. Further, one hollow rectangular gap layer made of a cardboard of $L_{15}$ 385 mm×$L_{16}$ 355 mm and having an average gap thickness of $L_{17}$ 75 mm was prepared. The density of the body fluid treatment device layer was 0.140 g/cm$^3$, the density of the gap layer was 0.015 g/cm$^3$, and an average density of the body fluid treatment device was 0.291 g/cm$^3$.

As illustrated in FIG. 9(a), both surfaces of the gap layer were sandwiched by the two body fluid treatment device layers to obtain a stack structure, and the stack structure was housed in a cardboard case of $L_{10}$ 422 mm×$L_{11}$ 365 mm×$L_{12}$ 240 mm to obtain a package. Of the 12 body fluid treatment devices in total, four body fluid treatment devices (indicated by the symbol "S") were used for measuring a dose distribution, and four body fluid treatment devices (indicated by the symbol "M") were used for measuring the material deterioration. Four packages were placed on an irradiation tray, and an electron beam with energy of 12 MeV was irradiated perpendicularly to the longitudinal direction of the body fluid treatment devices in an upward direction once. As a result of the measurement of an absorbed dose distribution, a maximum to minimum dose ratio was 1.862. An average PVP elution amount was 1.1 mg/module. Further, a vibration and drop test was performed in the packaged state. Consequently, a product was not damaged, a sterilization bag was not broken, and a hollow fiber membrane leakage did not occur. Each specification and the evaluation results are shown in Table 1.

Example 2

A body fluid treatment device of the same size as that in Example 1 was obtained under the same conditions as those in Example 1, except that the liquid adhesion rate was adjusted to 98%. Next, two body fluid treatment device layers were prepared, in which six body fluid treatment devices were arranged at equal intervals and substantially in parallel on a cardboard tray of $L_{13}$ 440 mm×$L_{14}$ 340 mm. Further, one hollow rectangular gap layer made of a cardboard of $L_{15}$ 440 mm×$L_{16}$ 340 mm and having an average gap thickness of $L_{17}$ 60 mm was prepared. The density of the body fluid treatment device layer was 0.121 g/cm$^3$, the density of the gap layer was 0.019 g/cm$^3$, and an average density of the body fluid treatment device was 0.261 g/cm$^3$.

As illustrated in FIG. 9(b), both surfaces of the gap layer were sandwiched by the two body fluid treatment device layers so as to achieve a zigzag arrangement, to thereby obtain a stack structure, and the stack structure was housed in a cardboard case of $L_{10}$ 450 mm×$L_{11}$ 355 mm×$L_{12}$ 225 mm to obtain a package. Of the 12 body fluid treatment devices in total, four body fluid treatment devices (indicated by the symbol "S") were used for measuring a dose distribution, and four body fluid treatment devices (indicated by the symbol "M") were used for measuring the material deterioration.

One package was placed on an irradiation tray, and an electron beam with energy of 12 MeV was irradiated perpendicularly to the longitudinal direction of the body fluid treatment devices twice in total, once in an upward direction and once in a downward direction. As a result of the measurement of an absorbed dose distribution, a maximum to minimum dose ratio was 1.314. An average PVP elution amount was 1.1 mg/module. Each specification and the evaluation results are shown in Table 1.

Example 3

A body fluid treatment device was obtained under the same conditions as those in Example 1, except that a bundle of about 10,000 hollow fiber polysulfone-PVP based dialysis membranes were set as a separation material, the liquid adhesion rate was adjusted to 79%, and the body fluid treatment device had a whole length of 334.8 mm, a minimum diameter (container body portion) of 37.6 mm, and a maximum diameter (header portion) of 50.2 mm.

Next, one body fluid treatment device layer was prepared, in which 10 body fluid treatment devices were arranged at equal intervals and substantially in parallel on a cardboard tray of $L_{13}$ 350 mm×$L_{14}$ 320 mm in two rows each having five devices, and one body fluid treatment device layer was prepared, in which five body fluid treatment devices were arranged at equal intervals and substantially in parallel on a cardboard tray of $L_{13}$ 350 mm×$L_{14}$ 320 mm. Further, one hollow rectangular gap layer made of a cardboard of $L_{15}$ 350 mm×$L_{16}$ 320 mm and having an average gap thickness of $L_{17}$ 35 mm was prepared. The density of the body fluid treatment device layer was 0.088 g/cm$^3$, the density of the gap layer was 0.154 g/cm$^3$, and an average density of the body fluid treatment device was 0.258 g/cm$^3$.

As illustrated in FIG. 9(c), both surfaces of the gap layer were sandwiched by the two body fluid treatment device layers to obtain a stack structure, and the stack structure was housed in a cardboard case of $L_{10}$ 363 mm×$L_{11}$ 335 mm×$L_{12}$ 245 mm to obtain a package. Of the 15 body fluid treatment devices in total, six body fluid treatment devices (indicated by the symbol "S") were used for measuring a dose distribution, and six body fluid treatment devices (indicated by the symbol "M") were used for measuring the material deterioration.

One package was placed on an irradiation tray, and an electron beam with energy of 12 MeV was irradiated perpendicularly to the longitudinal direction of the body fluid treatment devices twice in total, once in an upward direction and once in a downward direction. As a result of the measurement of an absorbed dose distribution, a maximum to minimum dose ratio was 1.597. An average PVP elution amount was 1.1 mg/module. Each specification and the evaluation results are shown in Table 1.

Example 4

A body fluid treatment device was obtained under the same conditions as those in Example 1, except that a bundle of about 7,000 hollow fiber polysulfone-PVP based dialysis membranes were set as a separation material, the liquid adhesion rate was adjusted to 53%, and the body fluid treatment device had a whole length of 334.4 nun, a minimum diameter (container body portion) of 30.9 mm, and a maximum diameter (header portion) of 46.8 mm.

Next, one body fluid treatment device layer was prepared, in which 10 body fluid treatment devices were arranged at equal intervals and substantially in parallel on a cardboard tray of $L_{13}$ 415 mm×$L_{14}$ 340 mm in two rows each having 5 devices in a zigzag manner, and one body fluid treatment device layer was prepared, in which 5 body fluid treatment devices were arranged at equal intervals and substantially in parallel on a cardboard tray of $L_{13}$ 415 mm×$L_{14}$ 340 mm. Further, one hollow rectangular gap layer made of a cardboard of $L_{15}$ 415 mm×$L_{16}$ 340 mm and having an average gap thickness of $L_{17}$ 90 mm was prepared. The density of the body fluid treatment device layer was 0.053 g/cm$^3$, the density of the gap layer was 0.012 g/cm$^3$, and an average density of the body fluid treatment device was 0.233 g/cm$^3$.

As illustrated in FIG. 9(d), both surfaces of the gap layer were sandwiched by the two body fluid treatment device layers to obtain a stack structure, and the stack structure was housed in a cardboard case of $L_{10}$ 422 mm×$L_{11}$ 353 mm×$L_{12}$ 270 mm to obtain a package. Of the 15 body fluid treatment devices in total, six body fluid treatment devices (indicated by the symbol "S") were used for measuring a dose distribution, and six body fluid treatment devices (indicated by the symbol "M") were used for measuring the material deterioration.

Four packages were placed on an irradiation tray, and an electron beam with energy of 12 MeV was irradiated perpendicularly to the longitudinal direction of the body fluid treatment devices twice in total, once in an upward direction and once in a downward direction. As a result of the measurement of an absorbed dose distribution, a maximum to minimum dose ratio was 1.784. An average PVP elution amount was 1.2 mg/module. Further, a vibration and drop test was performed in the packaged state. Consequently, a product was not damaged, a sterilization bag was not broken, and a hollow fiber membrane leakage did not occur. Each specification and the evaluation results are shown in Table 1.

Example 5

A body fluid treatment device was obtained under the same conditions as those in Example 1, except that a bundle of about 12,000 hollow fiber polysulfone-PVP based dialysis membranes were set as a separation material, the liquid adhesion rate was adjusted to 86%, and the body fluid treatment device had a whole length of 334.8 mm, a minimum diameter (container body portion) of 40.5 mm, and a maximum diameter (header portion) of 53.0 mm.

Next, four body fluid treatment device layers were prepared, in each of which six body fluid treatment devices were arranged at equal intervals and substantially in parallel on a cardboard tray of $L_{13}$ 380 mm×$L_{14}$ 350 mm. A symbol "S" in the layers indicates a body fluid treatment device used for measuring an absorbed dose distribution. Further, three hollow rectangular gap layers made of a cardboard of $L_{15}$ 380 mm×$L_{16}$ 350 mm and having an average gap thickness of $L_{17}$ 25 mm were prepared. The density of the body fluid treatment device layer was 0.112 g/cm$^3$, the density of the gap layer was 0.099 g/cm$^3$, and an average density of the body fluid treatment device was 0.257 g/cm$^3$.

As illustrated in FIG. 9(e), both surfaces of the respective gap layers were sandwiched by two body fluid treatment device layers to obtain a stack structure, and the stack structure was housed in a cardboard case of $L_{10}$ 397 mm×$L_{11}$ 363 mm×$L_{12}$ 325 mm to obtain a package.

Of the 24 body fluid treatment devices in total, eight body fluid treatment devices (indicated by the symbol "S") were used for measuring a dose distribution, and eight body fluid treatment devices (indicated by the symbol "M") were used for measuring the material deterioration.

One package was placed on an irradiation tray, and an electron beam with energy of 12 MeV was irradiated perpendicularly to the longitudinal direction of the body fluid treatment devices twice in total, once in an upward direction and once in a downward direction. As a result of the measurement of an absorbed dose distribution, a maximum to minimum dose ratio was 1.672. An average PVP elution amount was 1.2 mg/module. Each specification and the evaluation results are shown in Table 1.

Example 6

A body fluid treatment device of the same size as that in Example 1 was obtained under the same conditions as those in Example 1, except that the liquid adhesion rate was adjusted to 270%.

Next, two body fluid treatment device layers were prepared, in each of which 12 body fluid treatment devices were arranged at equal intervals and substantially in parallel on a cardboard tray of $L_{13}$ 440 mm×$L_{14}$ 340 mm in two rows each having six devices in a zigzag manner. Further, one hollow rectangular gap layer made of a cardboard of $L_{15}$ 440 mm×$L_{16}$ 340 mm and having an average gap thickness of $L_{17}$ 50 mm was prepared. The density of the body fluid treatment device layer was 0.127 g/cm$^3$, the density of the gap layer was 0.042 g/cm$^3$, and an average density of the body fluid treatment device was 0.311 g/cm$^3$.

As illustrated in FIG. 9(f), both surfaces of the gap layer were sandwiched by the two body fluid treatment device layers to obtain a stack structure, and the stack structure was housed in a cardboard case of $L_{10}$ 450 mm×$L_{11}$ 355 mm×$L_{12}$ 365 mm to obtain a package.

Of the 24 body fluid treatment devices in total, eight body fluid treatment devices (indicated by the symbol "S") were used for measuring a dose distribution, and eight body fluid treatment devices (indicated by the symbol "M") were used for measuring the material deterioration.

Four packages were placed on an irradiation tray, and an electron beam with energy of 12 MeV was irradiated perpendicularly to the longitudinal direction of the body fluid treatment devices twice in total, once in an upward direction and once in a downward direction. As a result of the measurement of an absorbed dose distribution, a maximum to minimum dose ratio was 1.990. An average PVP elution amount was 1.2 mg/module. Further, a vibration and drop test was performed in the packaged state. Consequently, a product was not damaged, a sterilization bag was not broken, and a hollow fiber membrane leakage did not occur. Each specification and the evaluation results are shown in Table 1.

Example 7

A body fluid treatment device was obtained under the same conditions as those in Example 1, except that a bundle of about 14,000 hollow fiber polysulfone-PVP based dialysis membranes were set as a separation material, the liquid adhesion rate was adjusted to 150%, and the body fluid treatment device had a whole length of 335.2 mm, a minimum diameter (container body portion) of 43.2 mm, and a maximum diameter (header portion) of 55.0 mm.

Next, one body fluid treatment device layer was prepared, in which 10 body fluid treatment devices were arranged at equal intervals and substantially in parallel on a cardboard tray of $L_{13}$ 375 mm×$L_{14}$ 340 mm in two rows each having five devices in a zigzag manner, and two body fluid treatment device layers were prepared, in each of which five body fluid treatment devices were arranged at equal intervals and substantially in parallel on a cardboard tray of $L_{13}$ 375 mm×$L_{14}$ 340 mm. Further, two hollow rectangular gap layers made of a cardboard of $L_{15}$ 375 mm×$L_{16}$ 340 mm and having an average gap thickness of $L_{17}$ 15 mm were prepared. The density of the body fluid treatment device layer was 0.097 g/cm$^3$, the density of the gap layer was 0.084 g/cm$^3$, and an average density of the body fluid treatment device was 0.283 g/cm$^3$.

As illustrated in FIG. 9(g), both surfaces of the respective gap layers were sandwiched by two body fluid treatment device layers to obtain a stack structure, and the stack structure was housed in a cardboard case of $L_{10}$ 390 mm×$L_{11}$ 355 mm×$L_{12}$ 295 mm to obtain a package. Of the 20 body fluid treatment devices in total, 8 body fluid treatment devices (indicated by the symbol "S") were used for measuring a dose distribution, and 8 body fluid treatment devices (indicated by the symbol "M") were used for measuring the material deterioration.

Four packages were placed on an irradiation tray, and an electron beam with energy of 12 MeV was irradiated perpendicularly to the longitudinal direction of the body fluid treatment devices twice in total, once in an upward direction and once in a downward direction. As a result of the measurement of an absorbed dose distribution, a maximum to minimum dose ratio was 1.889. An average PVP elution amount was 1.3 mg/module. Each specification and the evaluation results are shown in Table 1.

Example 8

A body fluid treatment device of the same size as that in Example 1 was obtained under the same conditions as those in Example 1, except that the liquid adhesion rate was adjusted to 297%.

Next, four body fluid treatment device layers were prepared, in each of which 12 body fluid treatment devices were arranged at equal intervals and substantially in parallel on a cardboard tray of $L_{13}$ 440 mm×$L_{14}$ 340 mm. Further, four hollow rectangular gap layers made of a cardboard of $L_{15}$ 440 mm×$L_{16}$ 340 mm and having an average gap thickness of $L_{17}$ 10 mm were prepared. The density of the body fluid treatment device layer was 0.189 g/cm$^3$, the density of the gap layer was 0.176 g/cm$^3$, and an average density of the body fluid treatment device was 0.319 g/cm$^3$.

As illustrated in FIG. 9(h), both surfaces of the respective gap layers were sandwiched by two body fluid treatment device layers to obtain a stack structure, and the stack structure was housed in a cardboard case of $L_{10}$ 450 mm×$L_{11}$ 355 mm×$L_{12}$ 345 mm to obtain a package. Of the 24 body fluid treatment devices in total, eight body fluid treatment devices (indicated by the symbol "S") were used for measuring a dose distribution, and eight body fluid treatment devices (indicated by the symbol "M") were used for measuring the material deterioration.

One package was placed on an irradiation tray, and an electron beam with energy of 12 MeV was irradiated perpendicularly to the longitudinal direction of the body fluid treatment devices twice in total, once in an upward direction and once in a downward direction. As a result of the measurement of an absorbed dose distribution, a maximum to minimum dose ratio was 1.997. An average PVP elution amount was 1.2 mg/module. Further, a vibration and drop test was performed in the packaged state. Consequently, a product was not damaged, a sterilization bag was not broken, and a hollow fiber membrane leakage did not occur. Each specification and the evaluation results are shown in Table 1.

Example 9

A body fluid treatment device of the same size as that in Example 1 was obtained under the same conditions as those in Example 1, except that the liquid adhesion rate was adjusted to 368%.

Next, two body fluid treatment device layers were prepared, in each of which 12 body fluid treatment devices were arranged at equal intervals and substantially in parallel on a cardboard tray of $L_{13}$ 440 mm×$L_{44}$ 340 mm in two rows each having six devices in a zigzag manner. Further, one hollow rectangular gap layer made of a cardboard of $L_{15}$ 440 mm×$L_{46}$ 340 mm and having an average gap thickness of $L_{17}$ 50 mm was prepared. The density of the body fluid treatment device layer was 0.142 g/cm$^3$, the density of the gap layer was 0.042 g/cm$^3$, and an average density of the body fluid treatment device was 0.342 g/cm$^3$.

As illustrated in FIG. 9(i), both surfaces of the gap layer were sandwiched by the two body fluid treatment device layers to obtain a stack structure, and the stack structure was housed in a cardboard case of $L_{10}$ 450 mm×$L_{11}$ 355 mm×$L_{12}$ 365 mm to obtain a package. Of the 24 body fluid treatment devices in total, eight body fluid treatment devices (indicated by the symbol "S") were used for measuring a dose distribution, and eight body fluid treatment devices (indicated by the symbol "M") were used for measuring the material deterioration.

Four packages were placed on an irradiation tray, and an electron beam with energy of 12 MeV was irradiated perpendicularly to the longitudinal direction of the body fluid treatment devices twice in total, once in an upward direction and once in a downward direction. As a result of the measurement of an absorbed dose distribution, a maximum to minimum dose ratio was 1.998. An average PVP elution amount was 1.1 mg/module. Each specification and the evaluation results are shown in Table 1.

Example 10

A bundle of about 16,000 hollow polysulfone-PVP based dialysis membranes were set as a separation material in a cylindrical resin container having two inlet and outlet ports for a fluid in the vicinity of both ends, and the both ends were subjected to potting with a urethane resin. A glycerin aqueous solution was injected from the ends, and a remaining fluid was blown away with compressed air to adjust the liquid adhesion rate of the membranes to 315%. After that, headers having liquid inlet and outlet ports were attached to both ends to obtain a body fluid treatment device. The body fluid treatment device had a whole length of 335.2 mm, a minimum diameter (container body portion) of 46.9 mm, and a maximum diameter (header portion) of 59.0 mm. The body fluid treatment devices were sealed in sterilization bags made of nylon/polyethylene one by one. At this time, as a body fluid treatment device for measuring a dose distribution, a body fluid treatment device illustrated in FIG. 4 was also prepared.

Figure 8:
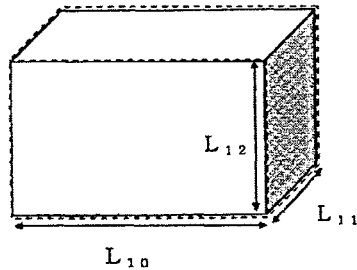
FIG. 8 is a schematic view illustrating positions for measuring the dimensions of the members used in Examples and Comparative Examples.
Figure 8:
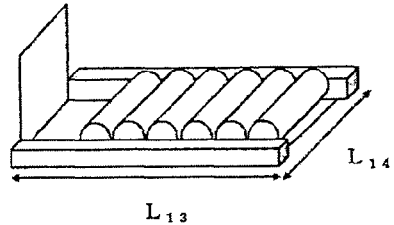
Figure 8:
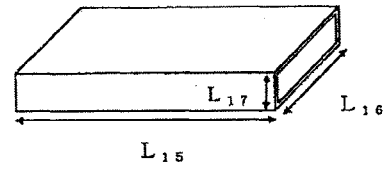

Next, four fluid treatment device layers were prepared, in each of which six body fluid treatment devices were arranged on a cardboard tray of $L_{13}$ 438 mm×$L_{14}$ 342 mm provided with the obstacle illustrated in FIG. 8(b). Next, as illustrated in FIG. 7, when each body fluid treatment device with a diameter "a" (59 mm) was arranged on a tray at equal intervals "b" (5 mm), and thicknesses "T" (9.5 mm) corresponding to an obstacle were provided at both ends of the tray, and a relationship between a distance "A" (76 mm) from the center of a circular cross-section of the body fluid treatment device at one end to the inner wall of one side at which the obstacle was provided in the tray and a distance "B" (44 mm) from the center of a circular cross-section of the body fluid treatment device at the other end to the inner wall of a side facing to the obstacle in the tray was A≠B. When the diameter of the body fluid treatment device was (a), the arrangement interval of the body fluid treatment devices was (b), the thickness of the obstacle was (T), and a constant (α) was 1.5, the distance A from the center of a circular cross-section of the body fluid treatment device at one end to the inner wall of one side at which the obstacle was provided in the tray was A=a+1.5b+T. The distance B from the center of the circular cross-section of the body fluid treatment device at the other end to the inner wall of the side facing to the obstacle in the tray was B=0.5a+b+T. Of the 24 body fluid treatment devices in total, eight body liquid treatment devices (indicated by the symbol "S") were used for measuring a dose distribution.

As illustrated in FIG. 9(j), a package unit to be stacked was inverted by 180° in the horizontal direction to the package unit placed immediately below, and housed sequentially in a cardboard case of $L_{10}$ 440 mm×$L_{11}$ 343 mm×$L_{12}$ 355 mm (inner size) to obtain a package in which four package units were stacked.

When the package units were stacked sequentially, an obstacle extending from the tray abutted on the inner wall of the cardboard case and rose to become an obstacle. Therefore, the package unit to be stacked subsequently could not be stacked smoothly in the case unless being inverted by 180°. As a result, the package units adjacent to each other were stacked easily without any mistake and trouble so that the circular cross-sections of the body fluid treatment devices were arranged in a zigzag manner with respect to each other.

Further, when the package units were stacked sequentially, one hollow rectangular solid (gap layer) made of a cardboard of $L_{15}$ 410 mm×$L_{16}$ 337 mm×$L_{17}$ 50 mm, as illustrated in FIG. 8(c), was stacked between the second and third package units to obtain a package (FIG. 9(b)). The density of the body fluid treatment device layer was 0.160 g/cm³, the density of the gap layer was 0.042 g/cm³, and the average density of the body fluid treatment device was 0.324 g/cm³.

Four packages were placed on an irradiation tray, and an electron beam with energy of 12 MeV was irradiated perpendicularly to the longitudinal direction of the body fluid treatment devices in an upward direction once. As a result of the measurement of an absorbed dose distribution, a maximum to minimum dose ratio was as remarkably small as 1.993. An average PVP elution amount was 1.1 mg/module. Each specification and the evaluation results are shown in Table 1.

By using the tray as in this example, when body fluid treatment devices are stacked to be packaged so as to be placed in a specified arrangement in a package, a stacking error of the package units may be prevented reliably while maintaining safety and ease. Thus, the body fluid treatment devices are stacked and arranged in a predetermined zigzag manner precisely in the package during packaging. As a result, electron beam irradiation sterilization may be performed without unevenness in an absorbed dose distribution, and further the workability and cost advantage may be remarkably improved. In addition, even if a package unit is stacked forcedly in a wrong manner, problems that a side surface of the packaging case is suddenly swollen by the obstacle or an upper cover cannot be closed may immediately be recognized by observation. Therefore, errors may be detected reliably before the completion of packaging, and the occurrence of a defective product may be prevented before happens.

Comparative Example 1

A body fluid treatment device of the same size as that in Example 1 was obtained under the same conditions as those in Example 1, except that the liquid adhesion rate was adjusted to 314%.

Next, four body fluid treatment device layers were prepared, in which 24 body fluid treatment devices were arranged at equal intervals and substantially in parallel on a cardboard tray of $L_{13}$ 440 mm×$L_{14}$ 340 mm. The density of the body fluid treatment device layer was 0.160 g/cm³ and an average density of the body fluid treatment device was 0.324 g/cm³.

As illustrated in FIG. 9(k), the four body fluid treatment device layers are stacked to obtain a stack structure, and the stack structure was housed in a cardboard case of $L_{10}$ 450 mm×$L_{11}$ 355 mm×$L_{12}$ 365 mm to obtain a package. Of the 24 body fluid treatment devices in total, eight body fluid treatment devices (indicated by the symbol "S") were used for measuring the dose distribution, and eight body fluid treatment devices (indicated by the symbol "M") were used for measuring the material deterioration.

Four packages were placed on an irradiation tray, and an electron beam with energy of 12 MeV was irradiated perpendicularly to the longitudinal direction of the body fluid treatment devices, once in an upward direction and once in a downward direction. As a result of the measurement of an absorbed dose distribution, a maximum to minimum dose ratio was 2.234. An average PVP elution amount was 2.5 mg/module. Further, a vibration and drop test was performed in the packaged state. Consequently, a product was not damaged and a hollow fiber membrane leakage did not occur, but a breakage of a sterilization bag occurred. Each specification and the evaluation results are shown in Table 2.

Comparative Example 2

A body fluid treatment device was obtained under the same conditions as those in Example 1, except that a bundle of about 12,000 hollow fiber polysulfone-PVP based dialysis membranes were set as a separation material, the liquid adhesion rate was adjusted to 157%, and the body fluid treatment device had a whole length of 334.8 mm, a minimum diameter (container body portion) of 40.5 mm, and a maximum diameter (header portion) of 53.0 mm.

Next, one body fluid treatment device layer was prepared, in which 12 body fluid treatment devices were arranged at equal intervals and substantially in parallel on a cardboard tray of $L_{13}$ 440 mm×$L_{14}$ 340 mm in two rows each having six devices. Further, one hollow rectangular gap layer made of a cardboard of $L_{15}$ 440 mm×$L_{16}$ 340 mm and having an average gap thickness of $L_{17}$ 50 mm was prepared. The density of the body fluid treatment device layer was 0.140 g/cm³, the density of the gap layer was 0.098 g/cm³, and an average density of the body fluid treatment device was 0.279 g/cm³.

As illustrated in FIG. 9(l), the gap layer was placed on the two body fluid treatment device layers to obtain a stack structure, and the stack structure was housed in a cardboard case of $L_{10}$ 422 mm×$L_{11}$ 353 mm×$L_{42}$ 210 mm to obtain a package. Of the 12 body fluid treatment devices in total, four body fluid treatment devices (indicated by the symbol "S") were used for measuring a dose distribution, and four body fluid treatment devices (indicated by the symbol "M") were used for measuring the material deterioration.

Four packages were placed on an irradiation tray, and an electron beam with energy of 12 MeV was irradiated perpendicularly to the longitudinal direction of the body fluid treatment devices in an upward direction once. As a result of the measurement of an absorbed dose distribution, a maximum to minimum dose ratio was 2.201. An average PVP elution amount was 2.3 mg/module. Each specification and the evaluation results are shown in Table 2.

Comparative Example 3

A body fluid treatment device was obtained under the same conditions as those in Example 1, except that a bundle of about 7,000 hollow fiber polysulfone-PVP based dialysis membranes were set as a separation material, the liquid adhesion rate was adjusted to 290%, and the body fluid treatment device had a whole length of 334.4 mm, a minimum diameter (container body portion) of 30.9 mm, and a maximum diameter (header portion) of 46.8 mm.

Next, two body fluid treatment device layers were prepared, in each of which 24 body fluid treatment devices were arranged at equal intervals and substantially in parallel on a cardboard tray of $L_{13}$ 440 mm×$L_{14}$ 340 mm in two rows each having six devices. Further, one hollow rectangular gap layer made of a cardboard of $L_{15}$ 440 mm×$L_{16}$ 340 mm and having an average gap thickness of $L_{17}$ 50 mm was prepared. The density of the body fluid treatment device layer was 0.178 g/cm³, the density of the gap layer was 0.190 g/cm³, and an average density of the body fluid treatment device was 0.317 g/cm³.

As illustrated in FIG. 9(m), both surfaces of the gap layer were sandwiched by the two body fluid treatment device layers to obtain a stack structure, and the stack structure was housed in a cardboard case of $L_{10}$ 422 mm×$L_{11}$ 353 mm×$L_{12}$ 363 mm to obtain a package. Of the 24 body fluid treatment devices in total, eight body fluid treatment devices (indicated by the symbol "S") were used for measuring a dose distribution, and eight body fluid treatment devices (indicated by the symbol "M") were used for measuring the material deterioration.

Four packages were placed on an irradiation tray, and an electron beam with energy of 12 MeV was irradiated perpendicularly to the longitudinal direction of the body fluid treatment devices twice in total, once in an upward direction and once in a downward direction. As a result of the measurement of an absorbed dose distribution, a maximum to minimum dose ratio was 2.541. An average PVP elution amount was 2.1 mg/module. Each specification and the evaluation results are shown in Table 2.

Comparative Example 4

A body fluid treatment device was obtained under the same conditions as those in Example 1, except that a bundle of about 7,000 hollow fiber polysulfone-PVP based dialysis membranes were set as a separation material, the liquid adhesion rate was adjusted to 5%, and the body fluid treatment device had a whole length of 292.0 mm, a minimum diameter (container body portion) of 35.0 mm, and a maximum diameter (header portion) of 43.1 mm.

Next, two body fluid treatment device layers were prepared, in each of which 24 body fluid treatment devices were arranged at equal intervals and substantially in parallel on a cardboard tray of $L_{13}$ 440 mm×$L_{14}$ 340 mm in two rows each having six devices. Further, one hollow rectangular gap layer made of a cardboard of $L_{15}$ 440 mm×$L_{16}$ 340 mm and having an average gap thickness of $L_{17}$ 50 mm was prepared. A symbol "S" in the layers indicates a body fluid treatment device for measuring an absorbed dose distribution. The density of the body fluid treatment device layer was 0.113 g/cm³, the density of the gap layer was 0.009 g/cm³, and an average density of the body fluid treatment devices was 0.178 g/cm³.

As illustrated in FIG. 9(n), both surfaces of the gap layer were sandwiched by the two body fluid treatment device layers to obtain a stack structure, and the stack structure was housed in a cardboard case of $L_{10}$ 422 mm×$L_{11}$ 353 mm×$L_{12}$ 363 mm to obtain a package. Of the 24 body fluid treatment devices in total, eight body fluid treatment devices (indicated by the symbol "S") were used for measuring a dose distribution, and eight body fluid treatment devices (indicated by the symbol "M") were used for measuring the material deterioration.

Four packages were placed on an irradiation tray, and an electron beam with energy of 12 MeV was irradiated perpendicularly to the longitudinal direction of the body fluid treatment devices twice in total, once in an upward direction and once in a downward direction. As a result of the measurement of an absorbed dose distribution, a maximum to minimum dose ratio was 1.980. An average PVP elution amount was 2.3 mg/module. Each specification and the evaluation results are shown in Table 2.

Comparative Example 5

A body fluid treatment device of the same size as that in Example 1 was obtained under the same conditions as those in Example 1, except that the liquid adhesion rate was adjusted to 298%. Next, two body fluid treatment device layers were prepared, in each of which 24 body fluid treatment devices were arranged at equal intervals and substantially in parallel on a cardboard tray of $L_{13}$ 440 mm×$L_{14}$ 340 mm in two rows each having six devices in a zigzag manner. A symbol "S" in the layers indicates a body fluid treatment device for measuring an absorbed dose distribution. Further, one hollow rectangular gap layer made of a cardboard of $L_{15}$ 440 mm×$L_{16}$ 340 mm and having an average gap thickness of $L_{17}$ 50 mm was prepared. The density of the body fluid treatment device layer was 0.221 g/cm³, the density of the gap layer was 0.163 g/cm³, and an average density of the body fluid treatment device was 0.319 g/cm³. As illustrated in FIG. 9(o), both surfaces of the gap layer were sandwiched by the two body fluid treatment device layers to obtain a stack structure, and the stack structure was housed in a cardboard case of $L_{10}$ 450 mm×$L_{11}$ 355 mm×$L_{12}$ 365 mm to obtain a package. Of the 24 body fluid treatment devices in total, eight body fluid treatment devices (indicated by the symbol "S") were used for measuring a dose distribution, and eight body fluid treatment devices (indicated by the symbol "M") were used for measuring the material deterioration.

Four packages were placed on an irradiation tray, and an electron beam with energy of 12 MeV was irradiated perpendicularly to the longitudinal direction of the body fluid treatment devices once in an upward direction. As a result of the measurement of an absorbed dose distribution, a maximum to minimum dose ratio was 2.785. An average PVP elution amount was 2.6 mg/module. Each specification and the evaluation results are shown in Table 2.

Comparative Example 6

A body fluid treatment device was obtained under the same conditions as those in Example 1, except that the liquid adhesion rate was adjusted to 4%.

Next, two body fluid treatment device layers were prepared, in each of which 24 body fluid treatment devices were arranged at equal intervals and substantially in parallel on a cardboard tray of $L_{13}$ 440 mm×$L_{14}$ 340 mm in two rows each having six devices. Further, one hollow rectangular gap layer made of a cardboard of $L_{15}$ 440 mm×$L_{16}$ 340 mm and having an average gap thickness of $L_{17}$ 50 mm was prepared. The density of the body fluid treatment device layer was 0.039 g/cm$^3$, the density of the gap layer was 0.190 g/cm$^3$, and an average density of the body fluid treatment device was 0.233 g/cm$^3$.

As illustrated in FIG. 9(p), both surfaces of the gap layer were sandwiched by the two body fluid treatment device layers to obtain a stack structure, and the stack structure was housed in a cardboard case of $L_{10}$ 450 mm×$L_{11}$ 355 mm×$L_{12}$ 365 mm to obtain a package. Of the 24 body fluid treatment devices in total, eight body fluid treatment devices (indicated by the symbol "S") were used for measuring a dose distribution, and eight body fluid treatment devices (indicated by the symbol "M") were used for measuring the material deterioration.

Four packages were placed on an irradiation tray, and an electron beam with energy of 12 MeV was irradiated perpendicularly to the longitudinal direction of the body fluid treatment devices twice in total, once in an upward direction and once in a downward direction. As a result of the measurement of an absorbed dose distribution, a maximum to minimum dose ratio was 1.961. An average PVP elution amount was 2.6 mg/module. Each specification and the evaluation results are shown in Table 2.

Comparative Example 7

A package was obtained by the same procedure as that in Example 10, except that, when four package units were stacked, a hollow rectangular solid (gap layer) made of a cardboard illustrated in FIG. 8(c) was not inserted between the second and third package units, and that the liquid adhesion rate was 314% (FIG. 9(q)). Further, of the 24 body fluid treatment devices in total, eight body fluid treatment devices (indicated by the symbol "S") were used for measuring a dose distribution, and eight body fluid treatment devices (indicated by the symbol "M") were used for measuring the material deterioration.

Four packages were placed on an irradiation tray, and an electron beam with energy of 12 MeV was irradiated perpendicularly to the longitudinal direction of the body fluid treatment devices in an upward direction once. The package units could be stacked easily without mistakes and without any trouble so that circular cross-sections of the body fluid treatment devices were arranged in a zigzag manner between adjacent package units. However, as a result of measuring an absorbed dose distribution, the maximum to minimum dose ratio was as high as 2.234 due to the absence of the gap layer. Further, as a result of performing a vibration and drop test under the packaged state, the product was not damaged and there was no hollow fiber membrane leakage, but a breakage of a sterilization bag occurred. Each specification and the evaluation results are shown in Table 2.

Comparative Example 8

Body fluid treatment devices were arranged in the same manner as in Comparative Example 7, except that four trays without obstacles of the cardboard trays of $L_{13}$ 438 mm×$L_{14}$ 342 mm provided with the obstacles illustrated in FIG. 5(a) were prepared and the liquid adhesion rate was 313%. Further, of 24 body fluid treatment devices, eight body fluid treatment devices (indicated by the symbol "S") were used for measuring a dose distribution and eight body fluid treatment devices (indicated by the symbol "M") were used for measuring the material deterioration.

As illustrated in FIG. 9(r), package units to be stacked were sequentially housed in a cardboard case of $L_{10}$ 450 mm×$L_{11}$ 355 mm×$L_{12}$ 365 mm (inner size) in the same direction as that of the package unit placed immediately below to obtain a package in which four package units were stacked. Further, when the package units were stacked sequentially, they were stacked smoothly in the case due to the absence of obstacles. However, because all the package units were stacked in the same direction, the circular cross-sections of the body fluid treatment devices were not arranged in a zigzag manner between the adjacent package units. This corresponds to a stacking error. Four packages were placed on an irradiation tray, and an electron beam with energy of 12 MeV was irradiated perpendicularly to the longitudinal direction of the body fluid treatment devices, once in an upward direction and once in a downward direction. All the package units were stacked in the same direction without being arranged in a zigzag manner, and hence, as a result of measuring an absorbed dose distribution, the maximum to minimum dose ratio was as high as 2.794, which was impermissible as non-uniformity of irradiation. Further, as a result of performing a vibration and drop test under the packaged state, the product was not damaged and there was no hollow fiber membrane leakage, but a breakage of a sterilization bag occurred. Each specification and the evaluation results are shown in Table 2.

TABLE 1

| | Example | | | | | | | | | |
|---|---|---|---|---|---|---|---|---|---|---|
| | 1 | 2 | 3 | 4 | 5 | 6 | 7 | 8 | 9 | 10 |
| Liquid adhesion rate (%) | 200 | 98 | 79 | 53 | 86 | 270 | 150 | 297 | 368 | 315 |
| Average gap thickness (mm) | 75 | 60 | 35 | 90 | 25 | 50 | 15 | 10 | 50 | 50 |
| Density of body fluid treatment layer (g/cm$^3$) | 0.140 | 0.121 | 0.088 | 0.053 | 0.112 | 0.127 | 0.097 | 0.189 | 0.142 | 0.160 |
| Density of gap layer (g/cm$^3$) | 0.015 | 0.019 | 0.154 | 0.012 | 0.099 | 0.042 | 0.084 | 0.176 | 0.042 | 0.042 |
| Average density of body fluid treatment device (g/cm$^3$) | 0.291 | 0.261 | 0.258 | 0.233 | 0.257 | 0.311 | 0.283 | 0.319 | 0.342 | 0.324 |
| Packaging efficiency (devices/m$^3$) | 3.7E-04 | 3.7E-04 | 3.4E-04 | 3.7E-04 | 4.7E-04 | 4.4E-04 | 4.7E-04 | 4.5E-04 | 4.4E-04 | 4.4E-04 |

TABLE 1-continued

| | Example | | | | | | | | | |
|---|---|---|---|---|---|---|---|---|---|---|
| | 1 | 2 | 3 | 4 | 5 | 6 | 7 | 8 | 9 | 10 |
| Maximum to minimum dose ratio | 1.862 | 1.314 | 1.597 | 1.784 | 1.672 | 1.990 | 1.889 | 1.997 | 1.998 | 1.993 |
| PVP elution amount (mg/module) | 1.1 | 1.1 | 1.1 | 1.2 | 1.2 | 1.2 | 1.3 | 1.2 | 1.1 | 1.1 |
| Oxygen concentration (%) | 21.9 | 0.95 | 21.9 | 21.9 | 21.9 | 21.9 | 21.9 | 21.9 | 21.9 | 21.9 |
| Ratio of gap layer | 0.536 | 0.429 | 0.292 | 0.900 | 0.250 | 0.357 | 0.125 | 0.071 | 0.357 | 0.357 |
| Vibration and drop test | No damage No bag breakage No leakage | — | — | No damage No bag breakage No leakage | — | No damage No bag breakage No leakage | — | No damage No bag breakage No leakage | — | — |

TABLE 2

| | Comparative Example | | | | | | | |
|---|---|---|---|---|---|---|---|---|
| | 1 | 2 | 3 | 4 | 5 | 6 | 7 | 8 |
| Liquid adhesion rate (%) | 314 | 157 | 290 | 5 | 298 | 4 | 314 | 313 |
| Average gap thickness (mm) | 0 | 50 | 50 | 50 | 50 | 50 | 50 | 50 |
| Density of body fluid treatment layer (g/cm$^3$) | 0.160 | 0.140 | 0.178 | 0.113 | 0.221 | 0.039 | 0.160 | 0.160 |
| Density of gap layer (g/cm$^3$) | 0 | 0.098 | 0.190 | 0.009 | 0.163 | 0.190 | 0 | 0 |
| Average density of body fluid treatment device (g/cm$^3$) | 0.324 | 0.279 | 0.317 | 0.178 | 0.319 | 0.233 | 0.324 | 0.324 |
| Packaging efficiency (devices/m$^3$) | 4.6E−04 | 4.8E−04 | 4.5E−04 | 4.5E−04 | 4.5E−04 | 4.5E−04 | 4.6E−04 | 4.6E−04 |
| Maximum to minimum dose ratio | 2.234 | 2.201 | 2.541 | 1.980 | 2.785 | 1.961 | 2.234 | 2.794 |
| PVP elution amount (mg/module) | 2.5 | 2.3 | 2.1 | 2.3 | 2.6 | 2.6 | 2.6 | 2.9 |
| Oxygen concentration (%) | 21.9 | 21.9 | 21.9 | 21.9 | 21.9 | 21.9 | 21.9 | 21.9 |
| Ratio of gap layer | 0 | 0.500 | 0.200 | 0.200 | 0.357 | 0.357 | 0 | 0 |
| Vibration and drop test | Bag broken No damage No leakage | — | — | — | — | — | Bag broken No damage No leakage | Bag broken No damage No leakage |

INDUSTRIAL APPLICABILITY

According to the sterilization method of the present invention, an electron beam may be irradiated even to medical supplies in a complicated shape such as body fluid treatment devices so that an absorbed dose distribution becomes small in each body fluid treatment device or among body fluid treatment devices in a case, as well as in one body fluid treatment device.

Thus, the sterilization method of the present invention is particularly preferred for a sterilization process of a mass-production type in which body liquid treatment devices are housed in a large amount in a case to pass through the production steps and to be distributed as a disposable type device.

The invention claimed is:

1. A method of sterilizing a plurality of dry or semi-dry body fluid treatment devices with a tubular shape that are housed in an electron beam-permeable case with an electron beam, comprising housing a stack structure in the electron beam-permeable case and thereafter irradiating with an electron beam: the stack structure comprising
   one gap layer with an average density of 0.010 to 0.180 g/cm$^3$; and
   two body fluid treatment device layers with an average density of 0.050 to 0.200 g/cm$^3$ in which both surfaces of the gap layer are sandwiched by the body fluid treatment device layers.

2. A method according to claim 1, wherein each of the body fluid treatment device layers has a configuration in which body fluid treatment devices are arranged substantially in parallel to each other in an axis direction, and arranged in one row or in a plurality of rows in a circular cross-sectional direction.

3. A method according to claim 1, wherein, on at least one of the body fluid treatment device layers of the stack structure, a gap layer and a body fluid treatment device layer are alternately stacked and housed in a case.

4. A method according to claim 1, wherein the case houses at least one stack structure.

5. A method according to claim 1, wherein, in the body fluid treatment device layers opposed to each other through the gap layer sandwiched therebetween, the body fluid treatment devices in the body fluid treatment layers are arranged in a zigzag manner in a circular cross-sectional direction.

6. A method according to claim 1, wherein, in one of the body fluid treatment device layers, the body fluid treatment devices in rows adjacent to each other are arranged in a zigzag manner in a circular cross-sectional direction.

7. A method according to claim 1, wherein an average thickness of the gap layer is 10 mm or more to 100 mm or less.

8. A method according to claim 1, wherein an average density of one or more body fluid treatment devices constituting the body fluid treatment device layers is 0.200 to 0.350 g/cm$^3$.

9. A method according to claim 1, wherein the body fluid treatment device in the tubular shape contains a separation material, and a liquid adhesion rate with respect to a dry weight of the separation material is 50 to 400%.

10. A method according to claim 9, wherein a wetting agent of the separation material is a mixture of water and a polyhydric alcohol.

11. A method according to claim 1, wherein the body fluid treatment device has a structure in which a hollow fiber membrane bundle made of a hydrophobic polymer and a hydrophilic polymer fills a container, an end of the bundle is held in the container by a potting layer to form a hollow fiber membrane inside chamber and a hollow fiber membrane outside chamber, the body fluid treatment device has a fluid inlet and outlet which communicate with the hollow fiber membrane inside chamber and another fluid inlet and outlet which communicate with the hollow fiber membrane outside chamber, and a space portion other than a portion occupied by the hollow fiber membrane bundle and fluid in the body fluid treatment device is occupied by gas with an oxygen concentration of 0.01% or more.

12. A method according to claim 11, wherein the gas that occupies the space portion other than the portion occupied by the hollow fiber membrane bundle and the fluid in the body fluid treatment device has substantially the same oxygen concentration as the atmosphere.

13. A method according to claim 1, comprising using a body fluid treatment device package unit as the body fluid treatment layer, wherein the body fluid treatment device package unit has a structure in which the body fluid treatment devices are fixed substantially parallel to each other in an axis direction on a rectangular electron beam-permeable tray and arranged in a row in a circular cross-sectional direction, at least a part of one side or adjacent two sides of the tray is provided with an obstacle capable of protruding perpendicularly to a horizontal surface of the tray, and a side opposed to the obstacle is provided with a cutout having a thickness equal to or larger than a thickness of the obstacle.

14. A method according to claim 13, wherein, in the package unit, the body fluid treatment devices are arranged at equal intervals on the tray, and a relationship between a distance "A" from a circular cross-section center of the body fluid treatment device at one end to an inner wall on one side at which the obstacle is provided in the tray, and a distance "B" from a circular cross-section center of the body fluid treatment device at another end to an inner wall on the side opposed to the obstacle in the tray is A≠B.

15. A method according to claim 14, wherein the distance "A" satisfies A=a+αb+T or A=0.5a+b+T, and the distance "B" satisfies B=0.5a+b+T or B=a+αb+T, wherein "a" is a diameter of the body fluid treatment device, "b" is an arrangement interval of the body fluid treatment devices, "T" is a thickness of the obstacle, and "α" is a constant, wherein the diameter "a" of the body fluid treatment device is 30 mm to 80 mm, the arrangement interval "b" of the body fluid treatment devices is 1 mm to 80 mm, the thickness "T" of the obstacle is 3 mm to 10 mm, and the constant "α" is 1.0 to 2.0.

16. A method according to claim 13, wherein, when a plurality of the package units are stacked in multiple layers in an electron beam-permeable rectangular packaging case, the package units are alternately stacked and packaged in the state that the obstacles provided to the package units are inverted by 180° in a horizontal direction.

17. A body fluid treatment device package sterilized with an electron beam by the method according to claim 1.

* * * * *